(12) United States Patent
Pellegrini

(10) Patent No.: US 11,475,753 B2
(45) Date of Patent: Oct. 18, 2022

(54) DEVICE FOR FACILITATING CORRECTING OF A POSTURE OF A USER

(71) Applicant: John Pellegrini, Placerville, CA (US)

(72) Inventor: John Pellegrini, Placerville, CA (US)

( * ) Notice: Subject to any disclaimer, the term of this patent is extended or adjusted under 35 U.S.C. 154(b) by 0 days.

(21) Appl. No.: 16/920,270

(22) Filed: Jul. 2, 2020

(65) Prior Publication Data

US 2021/0005070 A1     Jan. 7, 2021

Related U.S. Application Data

(60) Provisional application No. 62/869,947, filed on Jul. 2, 2019.

(51) Int. Cl.
     *G08B 21/04*      (2006.01)
     *G08B 21/18*      (2006.01)
     *G08B 6/00*      (2006.01)

(52) U.S. Cl.
     CPC ........... *G08B 21/0446* (2013.01); *G08B 6/00* (2013.01); *G08B 21/182* (2013.01)

(58) Field of Classification Search
     CPC .... G08B 21/0446; G08B 21/182; G08B 6/00; A61B 5/1116; A61B 5/4561
     See application file for complete search history.

(56) References Cited

U.S. PATENT DOCUMENTS

| | | | |
|---|---|---|---|
| 9,406,211 B2 | 8/2016 | Sahiholnasab et al. | |
| 9,795,322 B1 | 10/2017 | Karunaratne et al. | |
| 2007/0149360 A1* | 6/2007 | Narayanaswami | A63B 69/00 482/8 |
| 2013/0072820 A1* | 3/2013 | Lee | G06F 19/00 600/594 |
| 2014/0088607 A1 | 3/2014 | Recknor | |
| 2016/0045108 A1* | 2/2016 | Wu | A61B 3/112 351/210 |
| 2016/0140826 A1* | 5/2016 | Sahiholnasab | A61B 5/4561 340/573.7 |
| 2017/0290530 A1* | 10/2017 | Hong | A61B 5/1116 |
| 2019/0096224 A1 | 3/2019 | Shoham et al. | |
| 2020/0133450 A1* | 4/2020 | Lu | G06F 3/038 |

OTHER PUBLICATIONS

"Lumo Lift", https://www.amazon.com/Lumo-Lift-corrector-computers-Comfortable/dp/B00N9P8GMW.

* cited by examiner

*Primary Examiner* — Hongmin Fan

(57) ABSTRACT

Disclosed herein is a device comprising a user interface. The device is configured for facilitating correcting of a posture of a user based on an interaction between the user and the device through the user interface. Further, the device comprises at least one sensor configured for generating sensor data based on a spatial attribute of the device in relation to the user. Further, the device comprises a processing device configured for comparing the sensor data based on at least one predetermined criterion of the spatial attribute and generating a command based on the comparing of the sensor data. Further, the device comprises a storage device configured for storing the at least one predetermined criterion. Further, the device comprises an output indication device configured for generating at least one indication based on the command.

18 Claims, 45 Drawing Sheets

DEVICE FOR FACILITATING CORRECTING OF A POSTURE OF A USER

The current application claims a priority to the U.S. Provisional Patent application Ser. No. 62/869,947 filed on Jan. 1, 2014.

FIELD OF THE INVENTION

Generally, the present disclosure relates to the field of measurement devices. More specifically, the present disclosure relates to devices for facilitating correcting of a posture of a user based on an interaction between the user and the device through the user interface.

BACKGROUND OF THE INVENTION

Neck or cervical spine injuries are epidemics due to technologies that exist today such as smartphones and PDAs (ex. iPad®, mobile reading devices such as Kindle®, etc.). Smart Phones and PDAs are being used for hours with the neck in a forward bent position known medically as cervical flexion. The prolonged and repetitive downward flexed position of the neck causes micro-tears to the internal lower cervical disc. These micro-tears lead to disc pathologies such as protrusions and herniation. Some people have given it the term "Tech Neck". Further, some electronic devices describe an angle of use leading to a prolonged and repetitive downward flexed position of the neck of a user. However, devices that may be retrofitted or installed with all electronic devices, including tablet computers, smartphones, and so on do not exist. Further, existing devices do not correct the posture of the user.

Therefore, there is a need for improved devices for facilitating correcting of a posture of a user that may overcome one or more of the above-mentioned problems and/or limitations.

SUMMARY OF THE INVENTION

This summary is provided to introduce a selection of concepts in a simplified form, that are further described below in the Detailed Description. This summary is not intended to identify key features or essential features of the claimed subject matter. Nor is this summary intended to be used to limit the claimed subject matter's scope.

Disclosed herein is a device comprising a user interface. The device may be configured for facilitating correcting of a posture of a user based on an interaction between the user and the device through the user interface. Further, the interaction may facilitate communication between the device and the user through the user interface. Further, the device may include at least one sensor configured for generating sensor data based on a spatial attribute of the device in relation to the user. Further, the spatial attribute may include at least one of a spatial position of the device in relation to the user and a spatial orientation of the device in relation to the user. Further, the device may include a processing device communicatively coupled to the at least one sensor. Further, the processing device may be configured for comparing the sensor data based on at least one predetermined criterion of the spatial attribute and generating a command based on the comparing of the sensor data. Further, the device may include a storage device communicatively coupled with the processing device. Further, the storage device is configured for storing the at least one predetermined criterion. Further, the device may include an output indication device communicatively coupled with the processing device. Further, the output indication device may be configured for generating at least one indication based on the command According to some embodiments, a device comprising a user interface is disclosed. The device may be configured for facilitating correcting of a posture of a user based on an interaction of the user with the device through the user interface. Further, the interaction facilitates communication between the device and the user through the user interface. Further, the device may include at least one sensor configured for generating sensor data based on a spatial attribute of the device in relation to the user. Further, the spatial attribute may include at least one of a spatial position of the device in relation to the user and a spatial orientation of the device in relation to the user. Further, the device may include a processing device communicatively coupled to the at least one sensor. Further, the processing device may be configured for comparing the sensor data based on at least one predetermined criterion of the spatial attribute, generating a command based on the comparing of the sensor data, analyzing the sensor data, and generating at least one analytic data based on the analyzing. Further, the device may include a storage device communicatively coupled with the processing device. Further, the storage device may be configured for storing the at least one predetermined criterion of the spatial attribute. Further, the device may include a communication device communicatively coupled with the processing device. Further, the communication device may be configured for transmitting the at least one analytic data to at least one external device. Further, the device may include an output indication device communicatively coupled with the processing device. Further, the output indication device may be configured for generating at least one indication based on the command.

According to some embodiments, a portable electronic device comprising a display device is disclosed. Further, the portable device may be configured for facilitating correcting of a posture of a user based on an interaction between the user and the portable electronic device through the display device. Further, the interaction facilitates communication between the portable electronic device and the user through the display device. Further, the portable electronic device may include at least one sensor configured for generating sensor data based on an orientation of the device in relation to a horizontal level. Further, the orientation may include an angle of inclination in relation to the horizontal level. Further, the portable electronic device may include a processing device communicatively coupled to the at least one sensor. Further, the processing device may be configured for comparing the sensor data based on at least one predetermined orientation range. Further, the at least predetermined orientation range may be between 60 degrees of inclination in relation to the horizontal level and 90 degrees of inclination in relation to the horizontal level. Further, the processing device may be configured for generating a command based on the comparing of the sensor data. Further, the portable electronic device may include a storage device communicatively coupled with the processing device. Further, the storage device may be configured for storing the at least one predetermined orientation range. Further, the portable electronic device may include a haptic motor communicatively coupled with the processing device. Further, the haptic motor may be configured for generating vibration based on the command.

Both the foregoing summary and the following detailed description provide examples and are explanatory only. Accordingly, the foregoing summary and the following detailed description should not be considered to be restrictive. Further, features or variations may be provided in addition to those set forth herein. For example, embodiments may be directed to various feature combinations and sub-combinations described in the detailed description.

BRIEF DESCRIPTION OF DRAWINGS

The accompanying drawings, which are incorporated in and constitute a part of this disclosure, illustrate various embodiments of the present disclosure. The drawings contain representations of various trademarks and copyrights owned by the Applicants. In addition, the drawings may contain other marks owned by third parties and are being used for illustrative purposes only. All rights to various trademarks and copyrights represented herein, except those belonging to their respective owners, are vested in and the property of the applicants. The applicants retain and reserve all rights in their trademarks and copyrights included herein, and grant permission to reproduce the material only in connection with reproduction of the granted patent and for no other purpose.

Furthermore, the drawings may contain text or captions that may explain certain embodiments of the present disclosure. This text is included for illustrative, non-limiting, explanatory purposes of certain embodiments detailed in the present disclosure.

DETAILED DESCRIPTION

Figure 1:
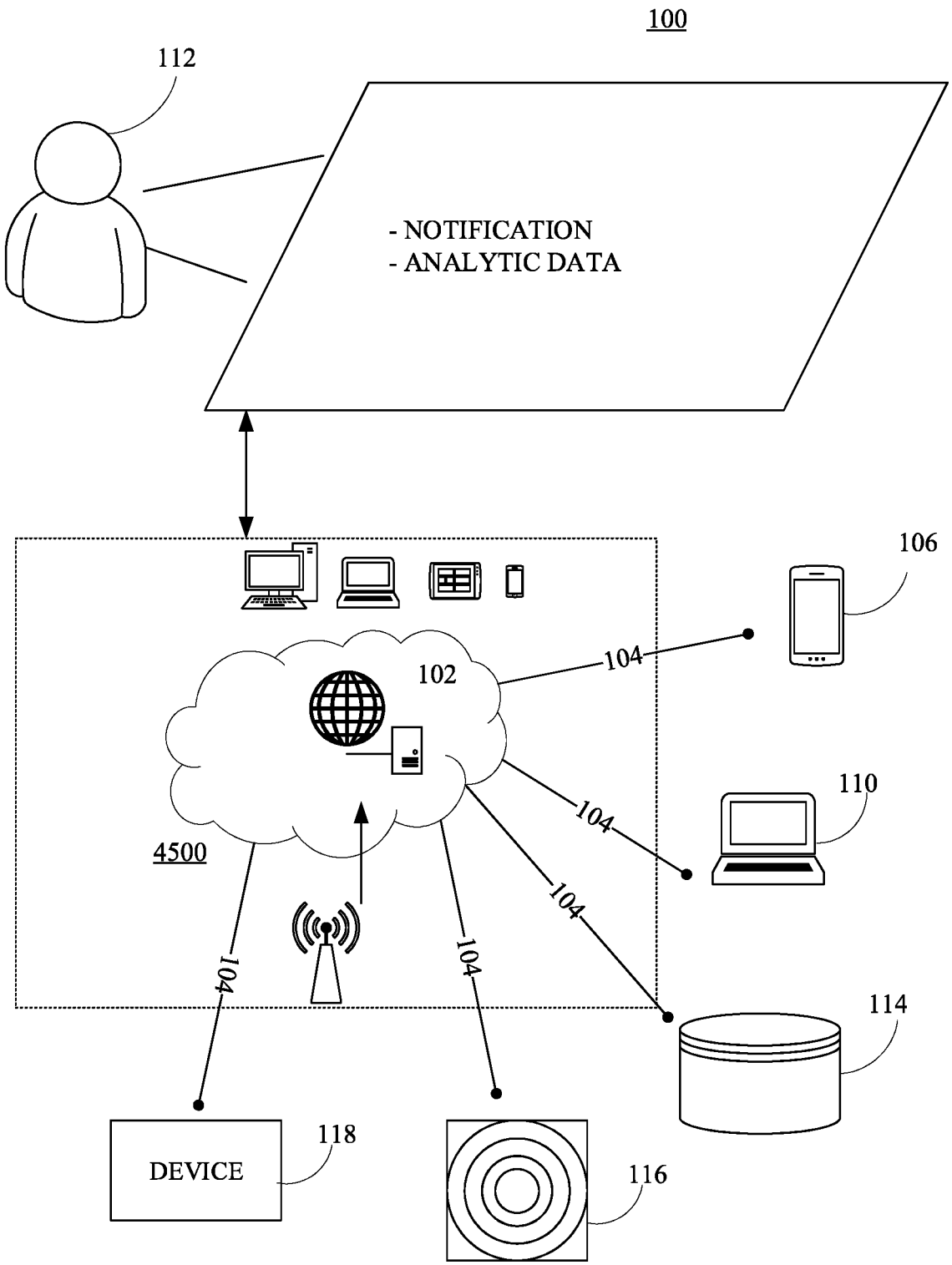
FIG. 1 is an illustration of an online platform consistent with various embodiments of the present disclosure.

As a preliminary matter, it will readily be understood by one having ordinary skill in the relevant art that the present disclosure has broad utility and application. As should be understood, any embodiment may incorporate only one or a plurality of the above-disclosed aspects of the disclosure and may further incorporate only one or a plurality of the above-disclosed features. Furthermore, any embodiment discussed and identified as being "preferred" is considered to be part of a best mode contemplated for carrying out the embodiments of the present disclosure. Other embodiments also may be discussed for additional illustrative purposes in providing a full and enabling disclosure. Moreover, many embodiments, such as adaptations, variations, modifications, and equivalent arrangements, will be implicitly disclosed by the embodiments described herein and fall within the scope of the present disclosure.

Accordingly, while embodiments are described herein in detail in relation to one or more embodiments, it is to be understood that this disclosure is illustrative and exemplary of the present disclosure, and are made merely for the purposes of providing a full and enabling disclosure. The detailed disclosure herein of one or more embodiments is not intended, nor is to be construed, to limit the scope of patent protection afforded in any claim of a patent issuing here from, which scope is to be defined by the claims and the equivalents thereof. It is not intended that the scope of patent protection be defined by reading into any claim limitation found herein and/or issuing here from that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present disclosure. Accordingly, it is intended that the scope of patent protection is to be defined by the issued claim(s) rather than the description set forth herein.

Additionally, it is important to note that each term used herein refers to that which an ordinary artisan would understand such term to mean based on the contextual use of such term herein. To the extent that the meaning of a term used herein—as understood by the ordinary artisan based on the contextual use of such term—differs in any way from any particular dictionary definition of such term, it is intended that the meaning of the term as understood by the ordinary artisan should prevail.

Furthermore, it is important to note that, as used herein, "a" and "an" each generally denotes "at least one," but does not exclude a plurality unless the contextual use dictates otherwise. When used herein to join a list of items, "or" denotes "at least one of the items," but does not exclude a plurality of items of the list. Finally, when used herein to join a list of items, "and" denotes "all of the items of the list."

The following detailed description refers to the accompanying drawings. Wherever possible, the same reference numbers are used in the drawings and the following description to refer to the same or similar elements. While many embodiments of the disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the disclosure. Instead, the proper scope of the disclosure is defined by the claims found herein and/or issuing here from. The present disclosure contains headers. It should be understood that these headers are used as references and are not to be construed as limiting upon the subjected matter disclosed under the header.

The present disclosure includes many aspects and features. Moreover, while many aspects and features relate to, and are described in the context of devices configured for facilitating correcting of a posture of a user, embodiments of the present disclosure are not limited to use only in this context.

Overview:

The present disclosure relates to a system for measuring the orientation of an electronic display device to aid in the correction of a viewing position of a user.

According to some embodiments, a system for measuring the orientation of an electronic display device to aid in the correction of a viewing position of a user, is disclosed. In some embodiments, the system may include a sensory device and an output indication device. Further, the sensory device may include an inclinometer sensor switch configured to sense the inclination of the electronic display device with respect to a horizontal level. Additionally, the sensory device may also include, but may not be limited to, a gravitational sensor, an accelerometer, a conductive inclination sensor, a micro electrochemical system, a gyroscope, and so on for measuring the angle of viewing of the electronic display device. In some embodiments, the inclinometer sensor may be electrically configured with an output indication device to transmit the sensory data from the inclinometer sensor to the output indicating device. In an instance, the indicating device may include a Light Emitting Diode (LED). Further, the LED may be placed on the left corner or the right corner of the electronic display device in accordance with the convenience of the user. In some embodiments, the LED may turn on when the electronic display device is in a flat or a horizontal position. Further, the LED may turn off when the electronic display device is tilted or moved to some vertical position, in an instance, a 60-degree angle with the horizontal level.

According to some embodiments, an external device to be placed on the body to provide additional information to the case or smartphone is disclosed. The external device (a measuring device) may be placed on the lower cervical spine and/or one at the Lumbar Spine (Low Back) which may use a tilt switch or a measuring device like a strain gauge to determine when the person was bent over into flexion (forward bending). The external device may be affixed to the skin by way of replaceable adhesive tape or other means such as a waist belt or belt clip.

This relates to the lower back because lower lumbar (Lower Back) disc injuries occur from repetitive bending forward form the waste. This flexion causes failure to the annulus of the disc which leads to acute lower back pain and possibly surgery. By having an additional device that is affixed to the lower back and has capabilities to communicate with the smartphone or smart case via Bluetooth, it may provide greater information on the lower back and possibly the neck.

Further, an ergonomic application is disclosed. The application may be able to position the person in the correct seat position as it relates to the height of their computer and arms distance to their computer. This may allow the person to set their ergonomic station. This may be accomplished simply by having the person take a selfie with their arms straight out in front. The smartphone with a smart case can be placed in the center of the laptop via a hook and the tilt angle would find the correct viewing angle of the computer screen. Once this is accomplished, the application may have a silhouette of the person that was obtained from the selfie taken. The individual may simply align their real image with the silhouette image with the phone camera. The calibrations programmed in the application may determine the correct height and distance so that the person could elevate their computer screen or move their computer closer/farther away. Further, it may be required to place something under their computer to achieve correct viewing height. Once the person finds the correct height and distance the application may give a signal, such as a thumb up (Corrected position) indicating the person has achieved the correct ergonomic setting.

According to some embodiments, an electronic device is disclosed based on the understanding that neck or cervical spine injuries are epidemics due to the technologies that exist today such as smartphones and PDAs. The smart phones and PDAs are being used for hours with the neck in a forward bent position known medically as cervical flexion. The prolonged and repetitive downward flexed position of the neck causes micro-tears to the internal lower cervical disc. These micro-tears lead to disc pathologies such as protrusions and herniation. Some people have given it the term "Tech Neck". The disclosed electronic device is a Biofeedback device designed to help the person elevate their arms so that they are not looking down in an extremely flexed forward bent position while they are using their Smartphone or PDA devices.

The disclosed electronic device includes very small inclinometer switches with electronics that will be inserted into a designed phone case. This requires some electronics to turn on and off a LED light at a specific angle. The LED light will be placed specifically at the right upper corner (presumably for right-handed individuals) and could be placed on the left upper corner or upper-middle position to accommodate others.

Figure 14:
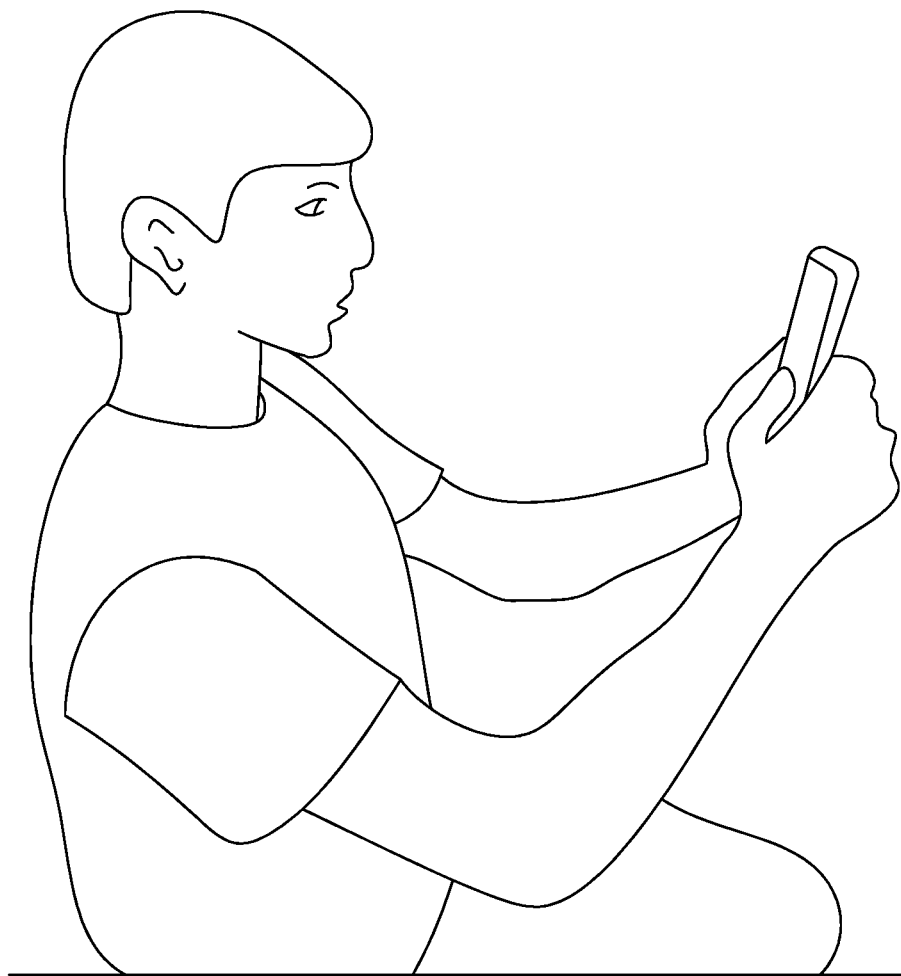
FIG. 14 shows a user using an electronic display device in correct posture.
Figure 15:
FIG. 15 shows a user using an electronic display device in correct posture.

When the person holds a phone flat on a table or horizontal it forces their neck to go into an extremely flexed position. This position is what causes neck injuries. By turning the disclosed electronic device, or Smart Case, on the light is turned on or the LED flashes when the phone is in the flat or horizontal position. As the phone and Smart Case are tilted to a more vertical position, such as a 60-degree angle, the LED will turn off. This will now let the individual know that they have their phone in the optimal position for viewing. Now that the phone is in the optimal angle, it will force the viewer to elevate their phone to have a better view. As the individual corrects their phone viewing angle, it will automatically place the viewer's neck in a less flexed position, thus resulting in reducing the pressure and stress to their lower cervical spine. The optimal angle for many individuals may be closer to 70-75 degrees. The disclosed electronic device may be configured to activate LED at any angle range from 50 degrees to 90 degrees. In an exemplary embodiment, the disclosed electronic device will have two angles that can be set. One angle may be at 60 degrees denoting a moderated degree of correction. A second angle may be at 75 degrees denoting a more advanced level of correction. The disclosed electronic device may include four inclinometer switches for a two-stage system. A second inclinometer switch is needed to accommodate the horizontal position as shown in FIG. 15. It is placed perpendicular to the first inclinometer switch (corresponding to FIG. 14). This creates a 90 angle by design and allows for a more streamline fit into the top corner of the phone case, thus allowing a more streamlined look to the cases.

The disclosed electronic device may be waterproof. Further, disclosed electronic device may use a 3 volt system or an induction battery that can be charged with phones that are using technologies such as induction charging phones or PDAs. This would allow for the device's battery to get charged at the same time as their phone by placing the charging device in a strategic spot near the back of the case. The power source may be a very tiny solar panel placed in the case. Further, the disclosed electronic device may use any suitable available power source.

The biofeedback may be provided using at least one light (LED), vibration, sound, and other forms of biofeedback.

Further, an external attachment to the phone is disclosed. The external attachment would not be placed into the phone case but could be attached to the phone by other means such as a magnet, etc. This external attachment could be placed on the back of the phone and use vibration or sound to give the biofeedback. A magnet may be place inside the PDA or phone case allowing for attachment of the device via magnet. This external attachment may use the same technology as stated above but it would not be directly inserted into the case.

Further, by designing a case that has a type of hook in the back of the case it could be placed on top of a laptop or computer screen to allow the viewer to angle their laptop or computer screen correctly, which will also allow for a more advantageous position of their cervical spine thus reducing injury.

Further, by creating an application and using facial recognition programing, a person would be able to attach their phone via hook to the top of the laptop or computer screen and use this case in conjunction with the application to create the perfect ergonomic self-set up. It would allow for the correct height and distance of the laptop or computer screen and the inclinometer in the phone case will allow for the correct viewing angle.

According to some embodiments, the disclosed electronic device may also perform ergonomic facial recognition that works in conjunction with the tilt (accelerometer) portion.

According to some embodiments, a parental monitoring capability may be incorporated into the disclosed application and the disclosed electronic device. This may allow the parent to get information sent to them from a device (child's) and statistical information will be sent to the parent's phone-PDA-computer via email or Bluetooth. It will also allow the parent to set up an alarm for child use causing a sustained vibration to the device as it is mounted to the child's phone or PDA.

Further, the disclosed electronic device may be removable so that it can be placed on a phone then replaced on another device such as a PDA.

Referring now to figures, FIG. 1 is an illustration of an online platform 100 consistent with various embodiments of the present disclosure. By way of non-limiting example, the online platform 100 to facilitate correcting of a posture of a user may be hosted on a centralized server 102, such as, for example, a cloud computing service. The centralized server 102 may communicate with other network entities, such as, for example, a mobile device 106 (such as a smartphone, a laptop, a tablet computer, etc.), other electronic devices 110 (such as desktop computers, server computers, etc.), databases 114, sensors 116, and a device 118 (such as the device 200, the device 600, and the portable electronic device 900) over a communication network 104, such as, but not limited to, the Internet. Further, users of the online platform 100 may include relevant parties such as, but not limited to, end-users, users, administrators, and so on. Accordingly, in some instances, electronic devices operated by the one or more relevant parties may be in communication with the platform 100.

A user 112, such as the one or more relevant parties, may access online platform 100 through a web-based software application or browser. The web-based software application may be embodied as, for example, but not be limited to, a website, a web application, a desktop application, and a mobile application compatible with a computing device 4500.

Figure 2:
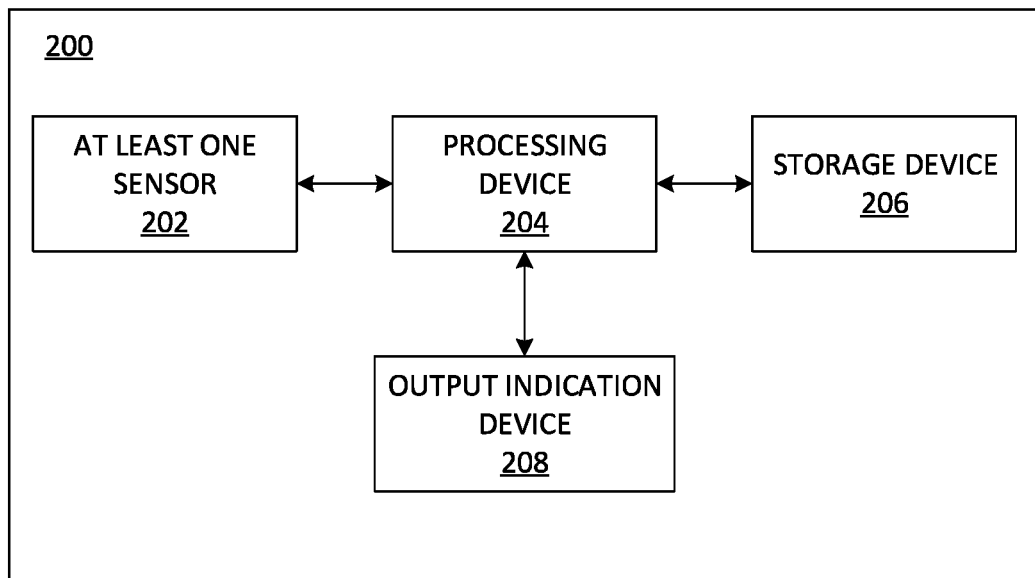
FIG. 2 is a block diagram of a device configured for facilitating correcting of a posture of a user based on an interaction of the user with the device through a user interface, in accordance with some embodiments.

FIG. 2 is a block diagram of a device 200 configured for facilitating correcting of a posture of a user (such as the user 112) based on an interaction between the user and the device 200 through a user interface, in accordance with some embodiments. The device 200 may include the user interface. Further, the interaction may facilitate communication between the device 200 and the user through the user interface. Further, the device 200 may include any electronic device such as an electronic reading device. Further, the device 200 may include any handheld device. Further, the device 200 may include any portable device. Further, the device 200 may include a computing device such as, but not limited to, a smartphone, a laptop, a tablet, a desktop, and so on. Further, the device 200 may include an exercise equipment such as, but not limited to, a treadmill, a gym-bike, and so on. Further, the device 200 may include an electronic display device such as, but not be limited to, a phone, an iPad®, a Kindle®, and so on. Further, the device 200 may be a non-electronic device such as a non-electronic reading device, a book, a table, and so on. Further, the interaction may include communication between the user and the device 200 such as but not limited to, viewing, displaying, presenting, capturing, sensing, and so on. Further, the user interface may include a display device, a capturing device, a sensing device, etc.

Further, the device 200 may include at least one sensor 202 (such as the sensors 116) configured for generating sensor data based on a spatial attribute of the device 200 in relation to the user. Further, the spatial attribute may include at least one of a spatial position of the device 200 in relation to the user and a spatial orientation of the device 200 in relation to the user. Further, the at least one sensor 202 may include an inclinometer sensor, a gravitational sensor, an accelerometer, a conductive inclination sensor, a gyroscope, etc. Further, the sensor data may be any data associated with the spatial attribute of the device 200. Further, the spatial attribute may include any attribute of the device 200 in a space. Further, the space may be a 1D space, a 2D, a 3D space, etc. Further, the attribute may include at least one of a position and an orientation of the device 200 in the space.

Further, the device 200 may include a processing device 204 communicatively coupled to the at least one sensor 202. Further, the processing device 204 may be configured for comparing the sensor data based on at least one predetermined criterion of the spatial attribute and generating a command based on the comparing of the sensor data. Further, the at least one predetermined criterion may include a predetermined vertical angle such as, but not limited to, a 60-degree angle with a horizontal level of the device 200. Further, the at least one predetermined criterion may include a range of angle of inclination from 60-degrees with the horizontal level to 90-degrees with the horizontal level.

Further, the device 200 may include a storage device 206 communicatively coupled with the processing device 204. Further, the storage device 206 is configured for storing the at least one predetermined criterion.

Further, the device 200 may include an output indication device 208 communicatively coupled with the processing device 204. Further, the output indication device 208 may be configured for generating at least one indication based on the command.

In some embodiments, the output indication device 208 may include at least one light-emitting device. Further, the at least one indication may include light. Further, the at least one light-emitting device is configured for generating the light based on the command.

In some embodiments, the output indication device 208 may include at least one haptic motor. Further, the at least one indication may include vibration. Further, the at least one haptic motor is configured for generating the vibration based on the command.

In some embodiments, the output indication device 208 may include at least one sound generating device. Further, the at least one indication may include sound. Further, the at least one sound generating device is configured for generating the sound based on the command.

In some embodiments, the at least one sensor 202 may be configured for generating first sensor data based on a user spatial attribute of the user in relation to the user interface. Further, the user spatial attribute may include at least one of a user position of the user in relation to the user interface and a user orientation of the user in relation to the user interface. Further, the processing device 204 is configured for determining a spatial relationship between the user and the user interface. Further, the generating of the command is based on the determining. Further, the first sensor data may be any data associated with the user spatial attribute of the user in relation to the user interface. Further, the user spatial attribute may include any attribute of the user in a space. Further, the space may be a 1D space, a 2D, a 3D space, etc. Further, the attribute may include at least one of a position and an orientation of the user in the space.

In further embodiments, the processing device 204 may be configured for generating a notification based on the determining. Further, the notification may include a correctness of the spatial relationship between the user and the user interface. Further, the user interface may include a presentation device (such as the mobile device 106, and the other electronic devices 110, etc.) configured for presenting the notification to the user. Further, the spatial relationship may include at least one of a position and an orientation of the user in a space in relation to the user interface. Further, the correctness of the spatial relationship corresponds to a value of at least one of the position and the orientation of the user. Further, the position may include a distance between the user and the user interface. Further, the correctness of the distance may include the value of the distance. Further, the orientation may include a viewing angle of the user in relation to the user interface. Further, the correctness of the viewing angle may include the value of the viewing angle. Further, the presentation device may include a display device, a microphone, a smartphone, a desktop, a laptop, a tablet, etc.

In further embodiments, the device 200 may include at least one dedicated mechanism detachably attached to the device 200. Further, the at least one dedicated mechanism may be configured for detachably attaching the device 200 to at least one object. Further, an object spatial attribute of the at least one object in relation to the user may correspond to the spatial attribute of the device 200. Further, the dedicated mechanism may include a metal piece and a magnet forming a hook. Further, the dedicated mechanism may include a clip acting as the hook. Further, the at least one object may include a laptop, a phone, an electronic reading device, a non-electronic reading device, a book, and so on. Further, the object spatial attribute may include any attribute of the object in a space. Further, the space may be a 1D space, a 2D, a 3D space, etc. Further, the attribute may include at least one of a position and an orientation of the object in the space.

Figure 3:
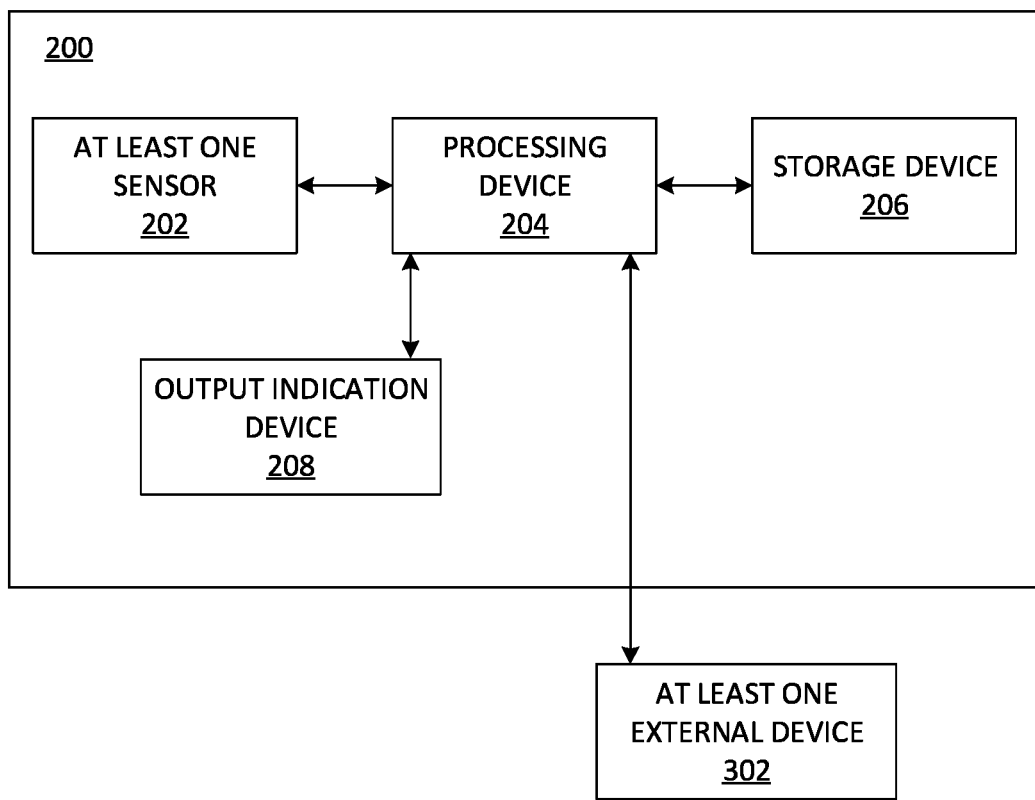
FIG. 3 is a block diagram of the device in accordance with further embodiments.

FIG. 3 is a block diagram of the device 200 in accordance with further embodiments. The device 200 may include at least one external device 302 coupled with the processing device 204. Further, the at least one external device 302 may be detachably attachable to at least one body part of the user using at least one attachment. Further, the at least one external device 302 may be configured for generating at least one information based on a posture of the user in relation to the user interface. Further, the processing device 204 may be configured for analyzing the at least one information and determining a correct posture of the user in relation to the user interface based on the analyzing of the at least one information. Further, the generating of the command may be based on the determining of the correct posture. Further, the at least one information may be any information associated with the posture of the user. Further, the information may include at least one of a position and an orientation of at least one body part of the user.

Figure 4:
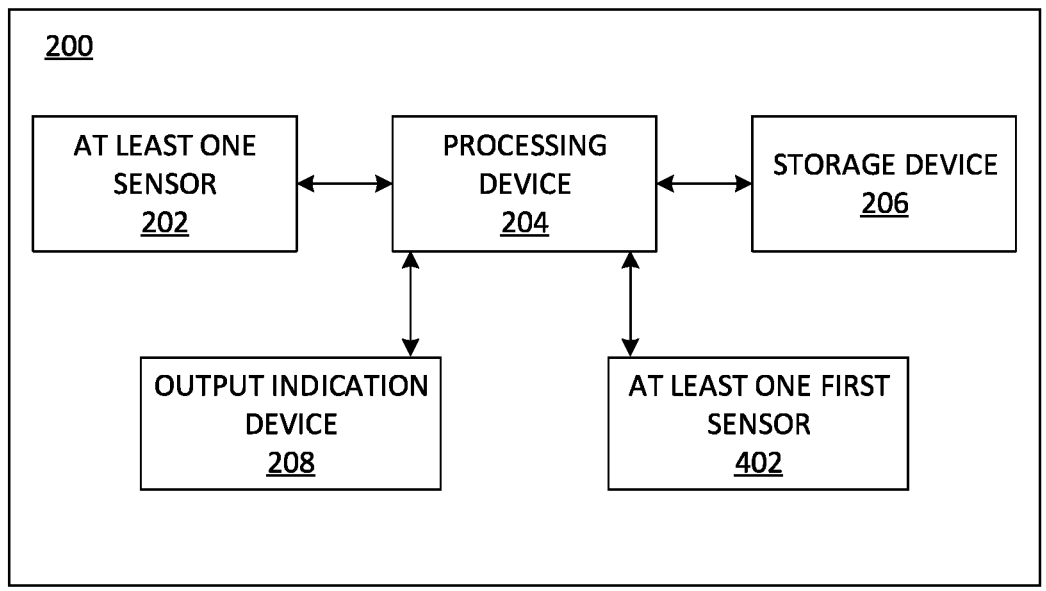
FIG. 4 is a block diagram of the device in accordance with further embodiments.

FIG. 4 is a block diagram of the device 200 in accordance with further embodiments. The device 200 may include at least one first sensor 402 (such as the sensors 116) communicatively coupled with the processing device 204. Further, the at least one first sensor 402 may be configured for generating second sensor data based on at least one action performed by the user. Further, the processing device 204 may be configured for analyzing the second sensor data and generating a first command based on the analyzing of the second sensor data. Further, the at least one sensor 202 may be associated with a first state and a second state. Further, the at least one sensor 202 may be configured for transitioning between the first state and the second state based on the first command. Further, the at least one sensor 202 may generate the sensor data in the first state and the at least one sensor 202 does not generate the sensor data in the second state. Further, the at least one first sensor 402 may include an inclinometer sensor, a gravitational sensor, an accelerometer, a conductive inclination sensor, a gyroscope, etc. Further, the second sensor data may be any data associated with the at least one action performed by the user. Further, the at least one action may include at least one movement performed by the user in relation to the at least one first sensor 402. Further, the first and the second state may be an operational state of the at least one sensor 202.

Figure 5:
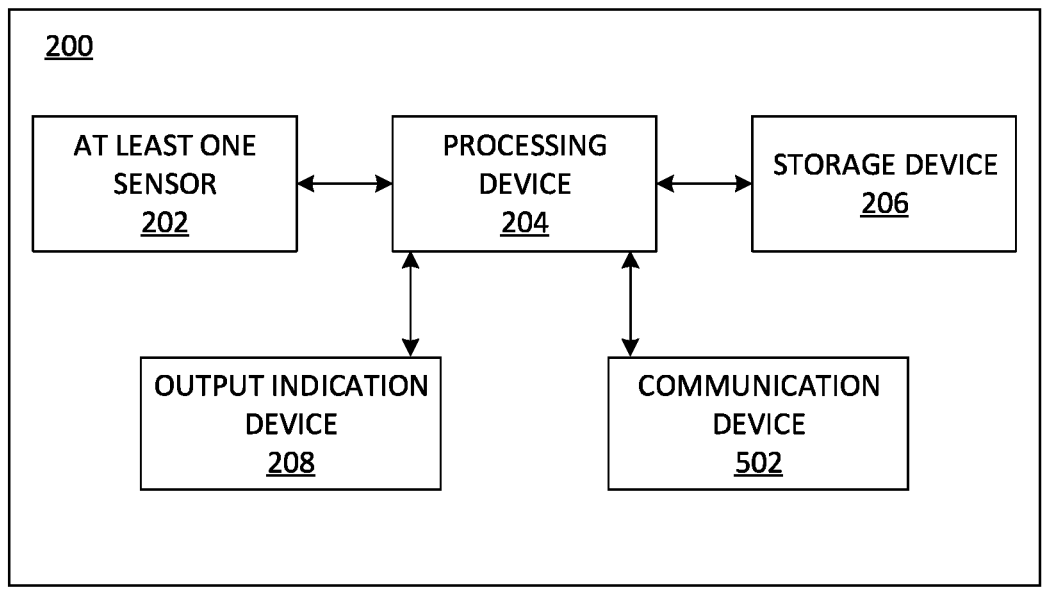
FIG. 5 is a block diagram of the device in accordance with further embodiments.

FIG. 5 is a block diagram of the device 200 in accordance with further embodiments. The device 200 may include a communication device 502 communicatively coupled with the processing device 204. Further, the communication device 502 may be configured for transmitting a plurality of questions to an output device of the user interface. Further, the communication device 502 may be configured for receiving a plurality of information corresponding to the plurality of questions from an input device of the user interface. Further, the processing device 204 may be configured for analyzing the plurality of information, determining at least one outcome based on the analyzing of the plurality of information, and generating the at least one predetermined criterion based on the determining. Further, the storing of the at least one predetermined criterion may be based on the generating of the at least one predetermined criterion. Further, the plurality of questions may be associated with at least one of a physiological state and a physical state of the user. Further, the plurality of questions may include a pain level, an area of pain, etc. Further, the at least one predetermined criterion may include an angle of activation, a strength of vibration, a pulse frequency of vibration, and a time of delay.

In some embodiments, the processing device 204 may be configured for analyzing the sensor data and generating at least one analytic data based on the analyzing. Further, the communication device 502 may be configured for transmitting the at least one analytic data to at least one external device (such as the mobile device 106, and the other electronic devices 110, etc.). Further, the at least one analytic data may include describing a postural behavior of the user. For instance, a time spent by the user in an incorrect viewing posture, and a correct viewing posture may be generated and may be represented through one or more visualizations, including graphs, charts, tables, and so on.

Figure 6:
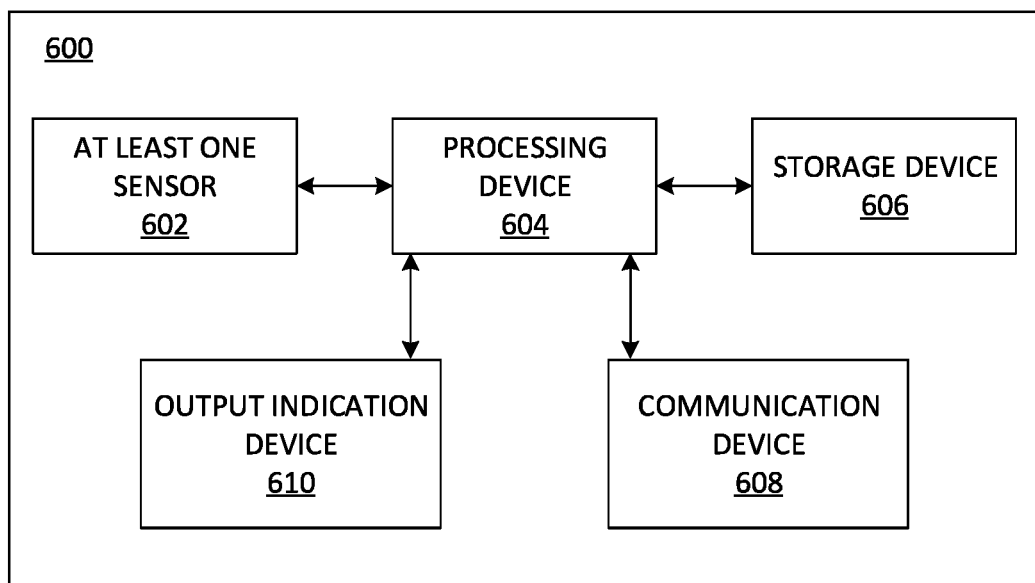
FIG. 6 is a block diagram of a device configured for facilitating correcting of a posture of a user based on an interaction of the user with the device through a user interface, in accordance with some embodiments.

FIG. 6 is a block diagram of a device 600 configured for facilitating correcting of a posture of a user based on an interaction between the user and the device 600 through a user interface, in accordance with some embodiments. Further, the device 600 may include the user interface. Further, the interaction may facilitate communication between the device 600 and the user through the user interface. Further, the device 600 may include any electronic device such as an electronic reading device. Further, the device 600 may include any handheld device. Further, the device 600 may include any portable device. Further, the device 600 may include a computing device such as, but not limited to, a smartphone, a laptop, a tablet, a desktop, and so on. Further, the device 600 may include an exercise equipment such as, but not limited to, a treadmill, a gym-bike, and so on.

Further, the device 600 may include an electronic display device such as, but not be limited to, a phone, an iPad®, a Kindle®, and so on. Further, the device 600 may be a non-electronic device such as a non-electronic reading device, a book, a table, and so on. Further, the interaction may include communication between the user and the device 600 such as but not limited to, viewing, displaying, presenting, capturing, sensing, and so on. Further, the user interface may include a display device, a capturing device, a sensing device, etc.

Further, the device 600 may include at least one sensor 602 (such as the sensor 116) configured for generating sensor data based on a spatial attribute of the device 600 in relation to the user. Further, the spatial attribute may include at least one of a spatial position of the device 600 in relation to the user and a spatial orientation of the device 600 in relation to the user. Further, the at least one sensor 602 may include an inclinometer sensor, a gravitational sensor, an accelerometer, a conductive inclination sensor, a gyroscope, etc. Further, the sensor data may be any data associated with the spatial attribute of the device 600. Further, the spatial attribute may include any attribute of the device 600 in a space. Further, the space may be a 1D space, a 2D, a 3D space, etc. Further, the attribute may include at least one of a position and an orientation of the device 600 in the space.

Further, the device 600 may include a processing device 604 communicatively coupled to the at least one sensor 602. Further, the processing device 604 is configured for comparing the sensor data based on at least one predetermined criterion of the spatial attribute, generating a command based on the comparing of the sensor data, analyzing the sensor data, and generating at least one analytic data based on the analyzing. Further, the at least one predetermined criterion may include a predetermined vertical angle such as, but not limited to, a 60-degree angle with a horizontal level of the device 600. Further, the at least one predetermined criterion may include a range of angle of inclination from 60-degrees with the horizontal level to 90-degrees with the horizontal level. Further, the at least one analytic data may include describing a postural behavior of the user. For instance, a time spent by the user in an incorrect viewing posture, and a correct viewing posture may be generated and may be represented through one or more visualizations, including graphs, charts, tables, and so on.

Further, the device 600 may include a storage device 606 communicatively coupled with the processing device 604. Further, the storage device 606 is configured for storing the at least one predetermined criterion of the spatial attribute.

Further, the device 600 may include a communication device 608 communicatively coupled with the processing device 604. Further, the communication device 608 is configured for transmitting the at least one analytic data to at least one external device (such as the mobile device 106, and the other electronic devices 110, etc.).

Further, the device 600 may include an output indication device 610 communicatively coupled with the processing device 604. Further, the output indication device 610 may be configured for generating at least one indication based on the command.

In some embodiments, the output indication device 610 may include at least one light-emitting device. Further, the at least one indication may include light. Further, the at least one light-emitting device may be configured for generating the light based on the command. In some embodiments, the output indication device 610 may include at least one haptic motor. Further, the at least one indication may include vibration. Further, the at least one haptic motor may be configured for generating the vibration based on the command.

In some embodiments, the output indication device 610 may include at least one sound generating device. Further, the at least one indication may include sound. Further, the at least one sound generating device is configured for generating the sound based on the command.

In some embodiments, the at least one sensor 602 is configured for generating first sensor data based on a user spatial attribute of the user in relation to the user interface. Further, the user spatial attribute may include at least one of a user position of the user in relation to the user interface and a user orientation of the user in relation to the user interface. Further, the processing device 604 is configured for determining a spatial relationship between the user and the user interface. Further, the generating of the command is based on the determining. Further, the first sensor data may be any data associated with the user spatial attribute of the user in relation to the user interface. Further, the user spatial attribute may include any attribute of the user in a space. Further, the space may be a 1D space, a 2D, a 3D space, etc. Further, the attribute may include at least one of a position and an orientation of the user in the space.

Figure 7:
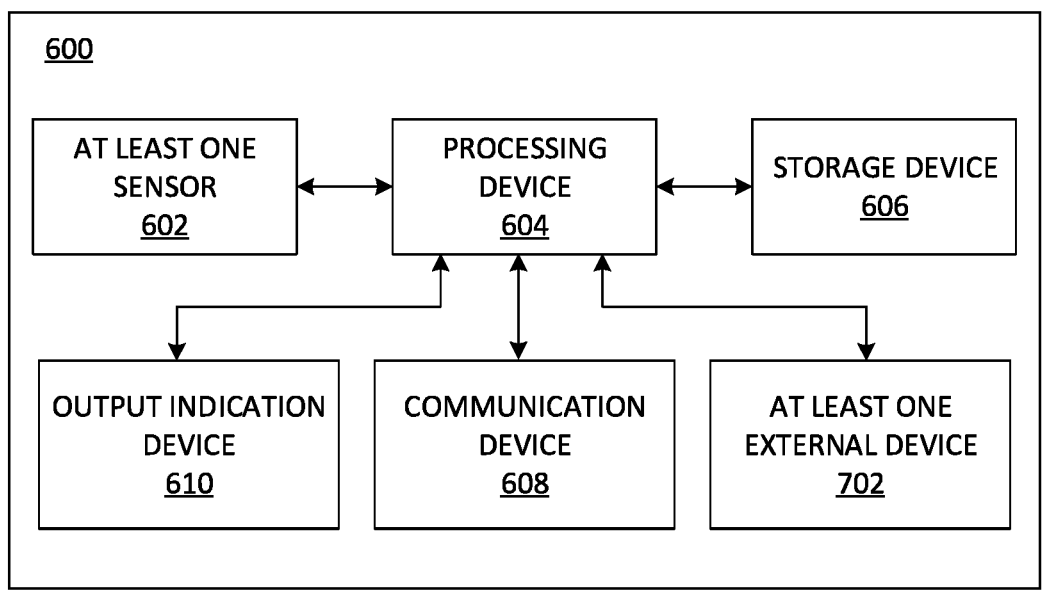
FIG. 7 is a block diagram of the device in accordance with some embodiments.

FIG. 7 is a block diagram of the device 600 in accordance with some embodiments. The device 600 may further include at least one external device 702 coupled with the processing device 604. Further, the at least one external device 702 may be configured for generating at least one information based on a posture of the user in relation to the user interface. Further, the processing device 604 may be configured for analyzing the at least one information and determining a correct posture of the user in relation to the user interface based on the analyzing of the at least one information. Further, the generating of the command is based on the determining of the correct posture.

Figure 8:
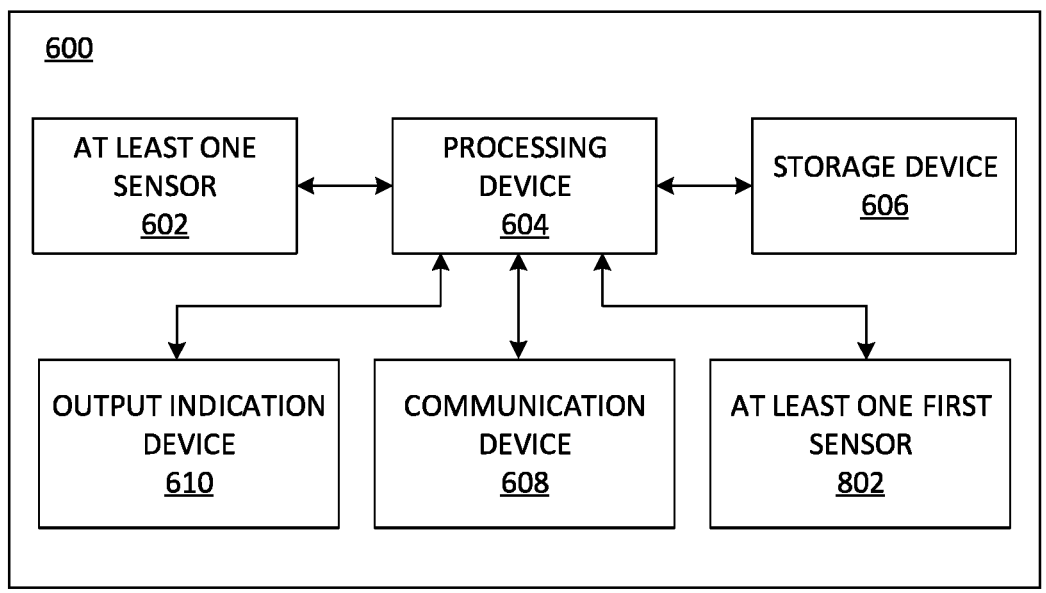
FIG. 8 is a block diagram of the device in accordance with some embodiments.

FIG. 8 is a block diagram of the device 600 in accordance with some embodiments. The device 600 may further include at least one first sensor 802 (such as the sensors 116) communicatively coupled with the processing device 604. Further, the at least one first sensor 802 may be configured for generating second sensor data based on at least one action performed by the user. Further, the processing device 604 may be configured for analyzing the second sensor data and generating a first command based on the analyzing of the second sensor data. Further, the at least one sensor 602 may be associated with a first state and a second state. Further, the at least one sensor 602 may be configured for transitioning between the first state and the second state based on the first command. Further, the at least one sensor 602 may generate the sensor data in the first state and the at least one sensor 602 does not generate the sensor data in the second state.

Figure 9:
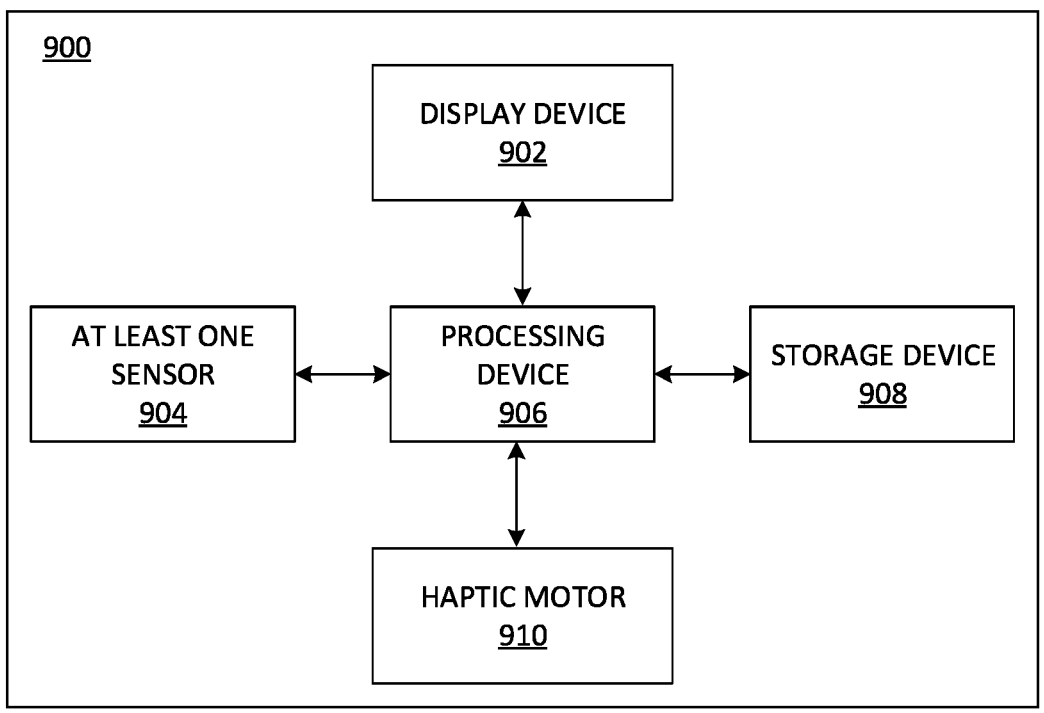
FIG. 9 is a block diagram of a portable electronic device configured for facilitating correcting of a posture of a user based on an interaction of the user with the device through a display device, in accordance with some embodiments.

FIG. 9 is a block diagram of a portable electronic device 900 configured for facilitating correcting of a posture of a user based on an interaction between the user and the portable electronic device 900 through a display device 902, in accordance with some embodiments. Further, the portable electronic device 900 may include the display device 902. Further, the interaction may facilitate communication between the portable electronic device 900 and the user through the display device 902. Further, the portable electronic device 900 may include a computing device such as, but not limited to, a smartphone, a laptop, a tablet, a desktop, and so on. Further, the communication between the user and the portable electronic device 900 may include viewing, displaying, presenting, capturing, sensing, etc.

Further, the portable electronic device 900 may include at least one sensor 904 (such as the sensors 116) configured for generating sensor data based on an orientation of the portable electronic device 900 in relation to a horizontal level. Further, the orientation may include an angle of inclination in relation to the horizontal level. Further, the at least one sensor 904 may include an inclinometer sensor, a gravitational sensor, an accelerometer, a conductive inclination sensor, a gyroscope, etc. Further, the sensor data may be any data associated with the spatial attribute of the portable electronic device 900. Further, the spatial attribute may include any attribute of the portable electronic device 900 in a space. Further, the space may be a 1D space, a 2D, a 3D space, etc. Further, the attribute may include at least one of a position and an orientation of the portable electronic device 900 in the space.

Further, the portable electronic device 900 may include a processing device 906 communicatively coupled to the at least one sensor 904. Further, the processing device 906 may be configured for comparing the sensor data based on at least one predetermined orientation range. Further, the at least predetermined orientation range may be between 60 degrees of inclination in relation to the horizontal level and 90 degrees of inclination in relation to the horizontal level. Further, the processing device 906 may be configured for generating a command based on the comparing of the sensor data.

Further, the portable electronic device 900 may include a storage device 908 communicatively coupled with the processing device 906. Further, the storage device 908 may be configured for storing the at least one predetermined orientation range.

Further, the portable electronic device 900 may include a haptic motor 910 communicatively coupled with the processing device 906. Further, the haptic motor 910 may be configured for generating vibration based on the command.

Figure 10:
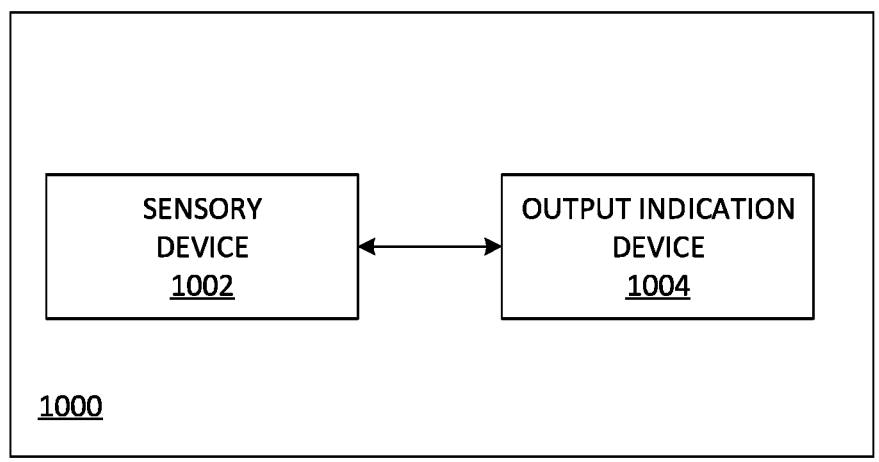
FIG. 10 is a block diagram of a system for measuring the orientation of an electronic display device to aid in the correction of a viewing position of a user, in accordance with some embodiments.

FIG. 10 is a block diagram of a system 1000 for measuring the orientation of an electronic display device to aid in the correction of a viewing position of a user, in accordance with some embodiments. In some embodiments, the system 1000 may include a sensory device 1002 and an output indication device 1004. Further, the sensory device 1002 may include an inclinometer sensor switch configured to sense the inclination of the electronic display device with respect to a horizontal level. Additionally, the sensory device 1002 may also include, but may not be limited to, a gravitational sensor, an accelerometer, a conductive inclination sensor, a micro-electrochemical system, a gyroscope, and so on for measuring the angle of viewing of the electronic display device. In an instance, the system 1000 may be incorporated into the electronic display device such as, but not be limited to, a phone, an iPad®, a Kindle®, and so on. Further, the electronic display device may include display devices related to gym equipment like a treadmill or a gym-bike. In some embodiments, the inclinometer sensor may communicate with the output indication device 1004 and may transmit the sensory data to the output indication device 1004. In an instance, the output indication device 1004 may include a Light Emitting Diode (LED). Further, the LED may be placed on the left corner or the right corner of the electronic display device in accordance with the convenience of the user. In some embodiments, the LED may turn on when the electronic display device is in a flat or a horizontal position. Further, the LED may turn off when the electronic display device may be tilted or moved to a predetermined vertical angle such as, but not limited to, a 60-degree angle with the horizontal level. In some embodiments, the angle of inclination of the electronic display device may exceed 60-degree and may be inclined up to 90-degrees.

Figure 13:
FIG. 13 shows a user using an electronic display device in an incorrect posture.

In some embodiments, the output indication device 1004 may include a haptic motor configured to provide vibration as an indication of the viewing angle. In an instance, the haptic motor may produce high vibration when the electronic device may be kept flat or horizontal to the surface. Further, in an instance, the haptic motor may produce low vibration when the electronic display device may be tilted to some angles. Finally, in an instance, the haptic motor may not produce vibration when the electronic display device may be tilted or inclined to predetermined angle, or a range thereof corresponding to an optimal viewing position of the user, such as between 60-degrees to 90-degrees from the horizontal level. In some embodiments, the haptic motor may produce vibration when the user uses the electronic display device in an incorrect posture as shown in FIG. 13. Further, in an instance, the output indication device 1004 may stop producing vibration when the user uses the electronic display device in a correct posture as shown in FIG. 14 and FIG. 15.

Further, in some embodiments, the output indication device 1004 may include a sound generating device to provide an indication of the viewing angle. In an instance, the sound generating device may include a single 555 IC microcontroller configured to generate a beep sound. In an instance, the beep sound may be high when the electronic device may be kept flat or horizontal to the surface. Further, the beep sound may be low when the electronic display device may be tilted to some angles. Finally, in an instance, the beep sound may stop when the electronic display device may be tilted or inclined to a predetermined angle, or a range thereof corresponding to an optimal viewing position of the user, such as between 60-degrees to 90-degrees from the horizontal level. In some embodiments, the output indication device 1004 may produce beep sound when the user uses the electronic display device in an incorrect posture as shown in FIG. 13. Further, in an instance, the output indication device 1004 may stop producing beep sound when the user uses the electronic display device in a correct posture as shown in FIG. 14 and FIG. 15. Accordingly, the system 1000 may allow the user to position the neck in a less flexed position while using the device, thereby reducing the causes of micro-tears to internal lower cervical disc and reducing injury. In an instance, the system 1000 may reduce the risks of road accidents.

Figure 11:
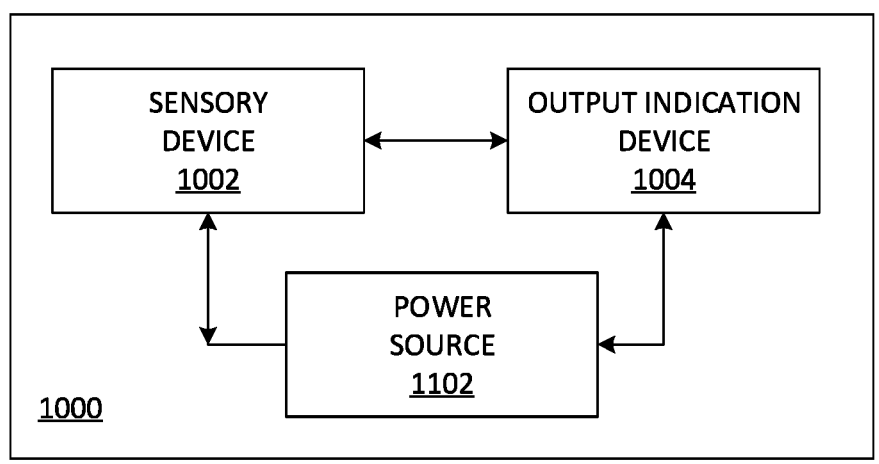
FIG. 11 is a block diagram of the system for measuring the orientation of an electronic display device to aid in the correction of a viewing position of a user, in accordance with further embodiments.

FIG. 11 is a block diagram of the system 1000 for measuring the orientation of an electronic display device to aid in the correction of a viewing position of a user, in accordance with further embodiments. In some embodiments, the system 1000 may include the sensory device 1002 to sense the inclination of the electronic display device from the horizontal level. Further, the sensory data may be transmitted to the output indication device 1004, such as a Light Emitting Diode (LED). In some embodiments, the output indication device 1004 may include a vibration or a sound generating device to indicate the correct viewing position of the electronic display device for the user. Further, the system 1000 may include a power source 1102 electrically coupled to each of the sensory device 1002 and the output indication device 1004. In an instance, the power source 1102 may include a 3-volt battery system. Further, the system 1000 may also include an induction battery that may be charged with the electronic display device itself. In an instance, the power source 1102 may include a solar power supply.

In some embodiments, the system 1000 may be an external attachment to the electronic display device. In an instance, the system 1000 may be attached to the electronic display device using a magnet. Further, in some embodiments, the magnet may be placed inside a casing of the electronic display device, such as a phone casing, to allow the attachment of the system 1000 to the electronic display device. Further, in an instance, one or more components of the system 1000 including the sensory device 1002, the output indication device 1004, and the power source 1102 may be included in an external protective case of for the electronic display device. For instance, the one or more components may be included in a protective case of a smartphone configured to be attached to the smartphone and measure the orientation of the smartphone to aid in the correction of a viewing position of a user. Further, in an instance, the power source 1102 may be configured to power the one or more components through solar energy as captured by a solar panel included in the external protective case of the electronic display device casing.

In some embodiments, the electronic device for the external protective case (a smart case) may have the ability to use Bluetooth technology to communicate with an application or computer software for data analysis. It may also have the ability to communicate with an external device such as a watch, Google Glass™, or other Bluetooth data logger devices for Biofeedback stimulus including but not limited to sound, vibration, and LED visual light.

In some embodiments, the system 1000 may be configured to communicate with an external device, such as a smartphone, a laptop, a tablet, and so on using wired connections such as micro-USB, USB-C, a lightning connector, and so on, and transmit the sensory data. In some embodiments, the system 1000 may be configured to communicate with an external device, such as a smartphone, a laptop, a tablet, and so on using a wireless connection, such as Bluetooth. Accordingly, the electronic display device may be configured to analyze the sensory data and generate analytics.

In some embodiments, the system 1000 may include a processing device, such as a processor to analyze the sensory data. Further, the system 1000 may be configured to transmit the analytics to the electronic display device, such as through a wired connection, or wirelessly.

In some embodiments, the analytics generated by the electronic display device may be viewed by the user using an application, such as a smartphone application, a webpage, and so on. Further, in an instance, the application may allow using the analytics generated by the electronic display device to aid in the correction of the viewing position of a user. For instance, the electronic display device may capture an image of the user upon detection of a correct and viewing position including an optimal viewing angle, and distance. Further, upon determination of a correct viewing angle, such as upon comparison of an image of the user captured while using the electronic display device, the electronic display device may indicate correctness of the viewing angle, such as by displaying a thumbs-up to the user through the application.

In some embodiments, a software application may be installed in the electronic display device such as, but not limited to, a smartphone, a laptop, a smartwatch, and so on. Further, the software application may be programmed to use the internal inclinometers, which may be inbuilt in the electronic display device, to determine the correct viewing position of the user. Further, the software application may provide an alert notification to the user whenever the user uses the electronic display device in an incorrect viewing position. Further, the alert notification may include a vibration or a beep sound to alert the user. Further, the vibration or the beep sound may stop when the user gets back the electronic display device to the correct viewing angle.

In some embodiments, the software application may allow the user to capture an image in the correct viewing angle. Further, the software application may compare the captured image against a posture of the user to determine the correct viewing angle which may aid in reducing a spinal disc pressure or musculoskeletal stress of the user. The software application may use a camera, which may be inbuilt in the electronic display device, to capture the image of the user.

In some embodiments, the system 1000 may communicate with the software application for analyzing the sensory data through a wireless connection such as, but not limited to, a Bluetooth, a Wi-Fi, and so on. Further, in some embodiments, the system 1000 may also communicate with an external device such as, but not limited to, a smartwatch, a Google Glass®, or other Bluetooth enabled devices. Further, the external device may be used as an output indication device 1004 to stimulate an indication such as, but not limited to a sound, a vibration, an LED visual light, and so on.

Figure 12:
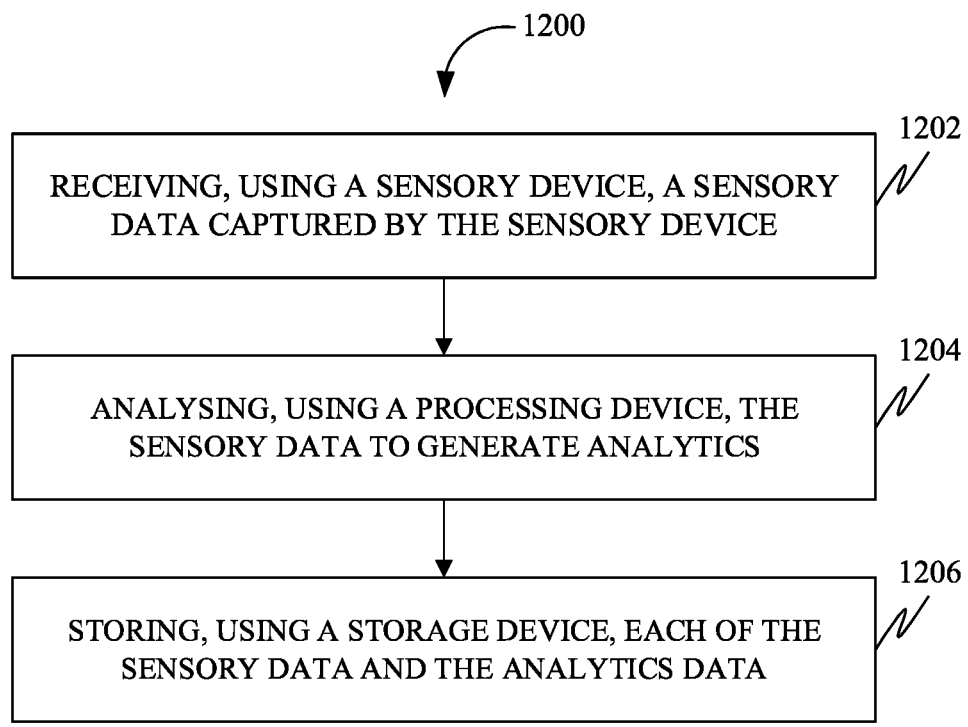
FIG. 12 is a flow chart of a method for measuring the orientation of an electronic display device to aid in the correction of a viewing position of a user, in accordance with some embodiments.

FIG. 12 is a flow chart of a method 1200 for measuring the orientation of an electronic display device to aid in the correction of a viewing position of a user, in accordance with some embodiments. At 1202, the method 1200 may include a step of receiving, using a sensory device, a sensory data captured by a sensory device. In some embodiments, the sensory device may include an inclinometer sensor to sense the orientation of the electronic display device. In some embodiments, the sensory device may also include, but may not be limited to, a gravitational sensor, an accelerometer, a conductive inclination sensor, a micro-electrochemical system, a gyroscope, and so on for measuring the angle of viewing of the electronic display device.

Further, at 1204, the method 1200 may include a step of analyzing, using a processing device, the sensory data to generate analytics. In some embodiments, the sensory data may include the angle of inclination of the electronic display device. In addition to the sensory data, time of each inclination angle may also be analyzed by the processing device. In some embodiments, the analyzing may include determining the posture of the user corresponding to the specific angle of inclination. In an instance, the angle of inclination equal to zero degrees may correspond to a forward bent position of the user. Further, the angle of inclination equal to 90-degrees may correspond to a straight upright position of the neck of the user. Further, the angle of inclination such as, but not limited to, 60, 70, or 80 degrees may correspond to a correct position of the neck of the user. In some embodiments, an optimal corrective angle may lie between 0-90 degrees. Further, the optimal corrective angle may relate to reducing spinal disc pressure and musculoskeletal stress. Further, the time elapsed in each posture of the user may also be analyzed by the processing device. In an instance, the analytics may include describing the postural behavior of the user. For instance, a time spent by the user in an incorrect viewing posture, and a correct viewing posture may be generated and may be represented through one or more visualizations, including graphs, charts, tables, and so on.

Further, at 1206, the method 1200 may include a step of storing, using a storage device, each of the sensory data, and the analytics data. In some embodiments, the sensory data received from the sensory device, and the analysis performed by the processing device may be stored for future references.

Figure 16:
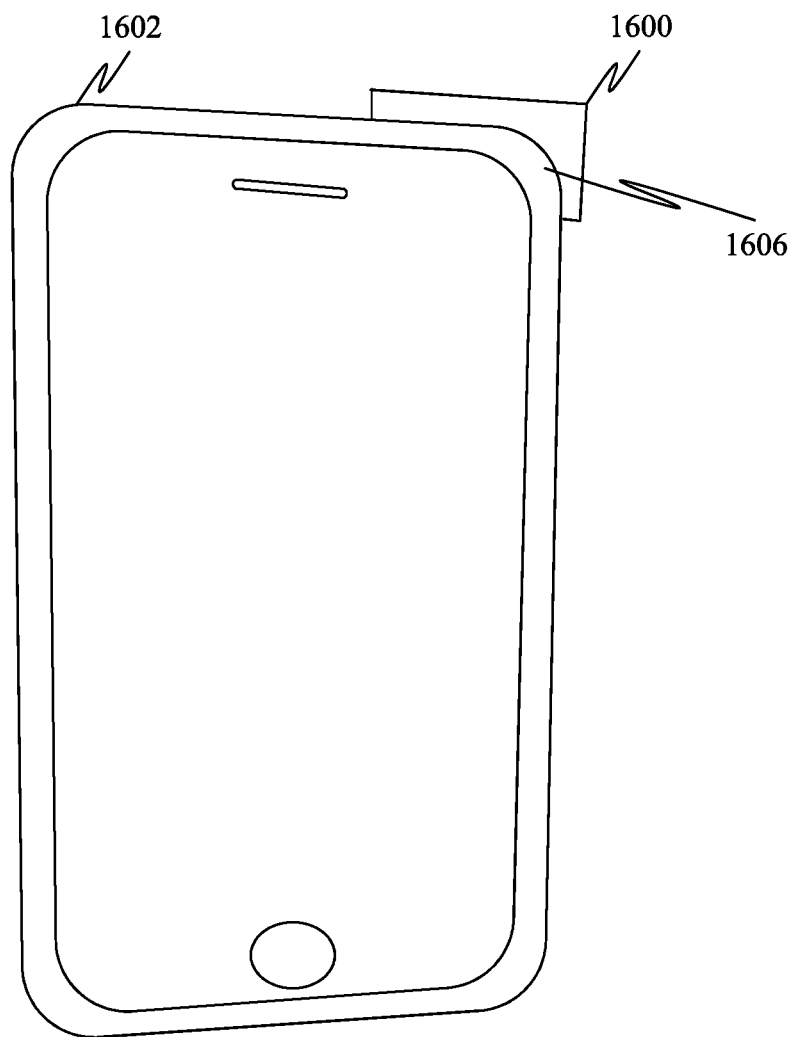
FIG. 16 is an exemplary representation of a system for measuring the orientation of an electronic display device to aid in the correction of a viewing position of a user, in accordance with some embodiments.

FIG. 16 is an exemplary representation of a system 1600 for measuring the orientation of an electronic display device 1602 to aid in the correction of a viewing position of a user, in accordance with some embodiments. In some embodiments, the system 1600 may be placed on a top corner 1606 of the electronic display device 1602. Further, in an embodiment, the system 1600 may be incorporated inside the electronic display device 1602. Further, the system 1600 may include an output indicating device, such as a Light Emitting Diode (LED). Further, the LED may be fixed on the top corner 1606 of the electronic display device 1602. In an instance, the LED may turn on when the electronic display device 1602 may be kept horizontal or flat to a surface. Further, the LED may turn off when the electronic display device 1602 may be tilted or oriented to a predetermined angle, or a range thereof corresponding to an optimal viewing position of the user, such as, but not be limited to between 60-degrees to 90-degrees from the horizontal level.

In some embodiments, the system 1600 may be attached to the top corner 1606 of a non-electronic book according to the convenience of a reader. In an instance, the system 1600 may include an LED as an output indicating device. Further, the output indicating device such as the LED may turn on when the non-electronic book may not be kept in a correct angle of viewing. Further, the LED may switch off when the non-electronic device may be kept in a correct angle of viewing such as, but not limited to, 60, 70, or 80 degrees. Further, the system 1600 may allow the reader to stay in a correct position while reading a non-electronic book.

Figure 17:
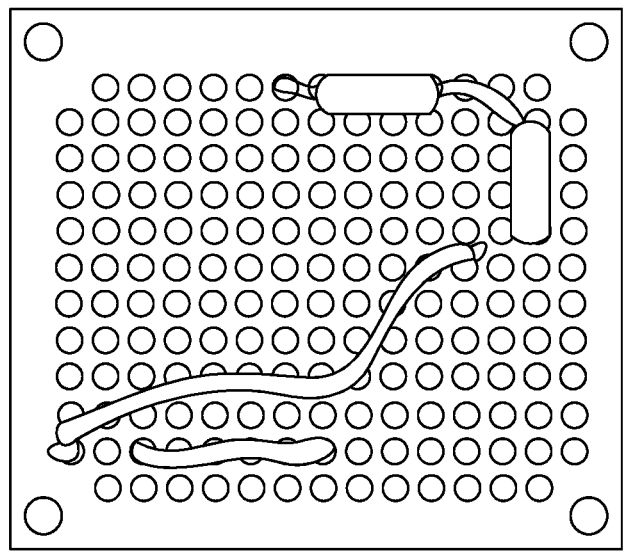
FIG. 17 is an exemplary representation of a working prototype of a system for measuring the orientation of an electronic display device to aid in the correction of a viewing position of a user, in accordance with some embodiments.

FIG. 17 is an exemplary representation of a working prototype of a system 1700 for measuring the orientation of an electronic display device to aid in the correction of a viewing position of a user, in accordance with some embodiments.

Figure 18:
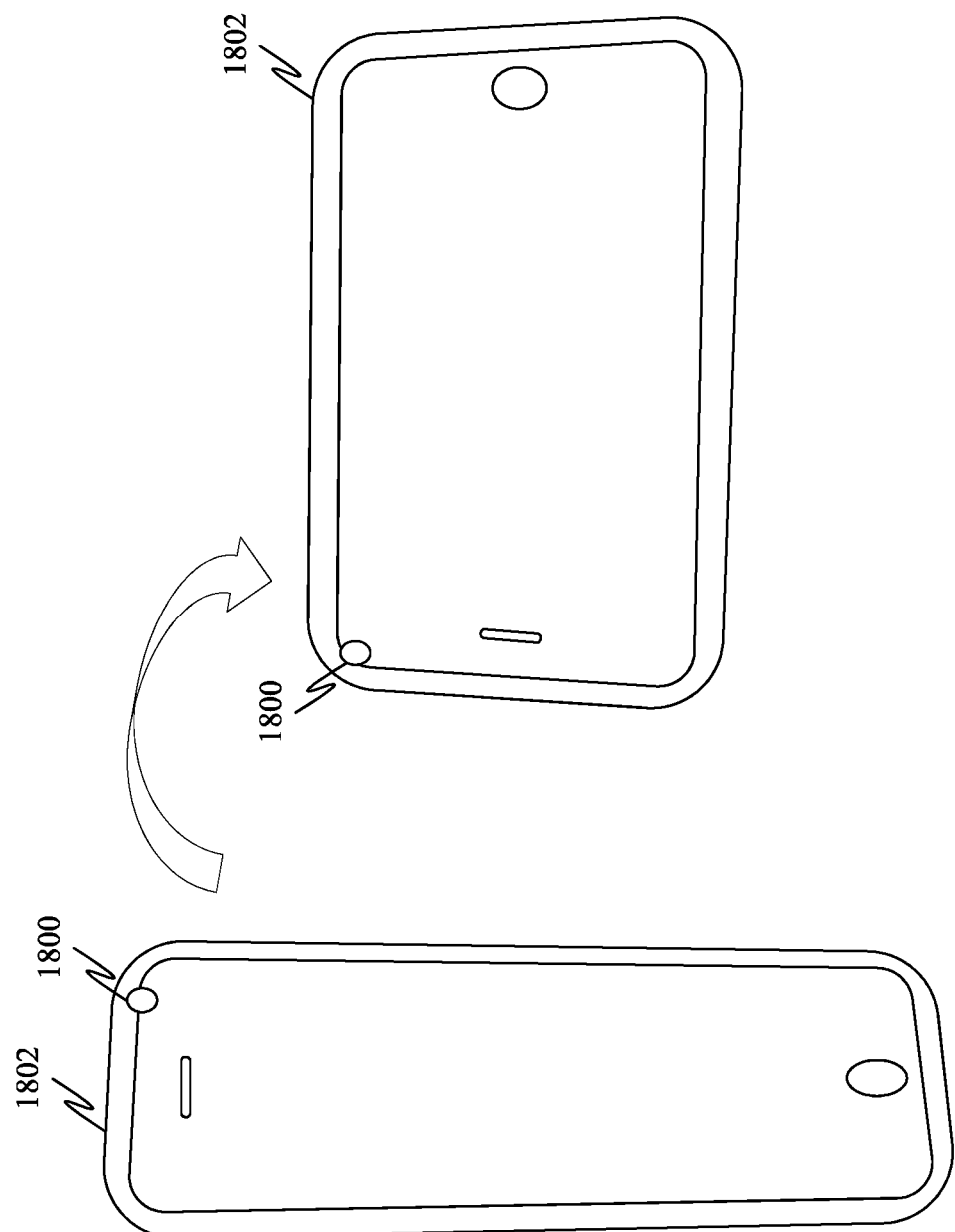
FIG. 18 is an exemplary representation of a system for measuring the orientation of an electronic display device to aid in the correction of a viewing position of a user, in accordance with some embodiments.

FIG. 18 is an exemplary representation of a system for measuring the orientation of an electronic display device 1802 to aid in the correction of a viewing position of a user, in accordance with some embodiments. In some embodiments, the system may include a sensory device to sense the orientation of the electronic display device 1802. Further, the system may also include an output indicating device 1800 to alert the user whenever the user may use the electronic display device 1802 in an incorrect posture. In an instance, the system may be designed to allow the user to rotate the electronic display device 1802 in both horizontal and vertical positions. Further, the system allows the electronic display device 1802 to switch between landscape and portrait mode without interruption.

In an embodiment, the output indicating device 1800 may be placed in the upper right corner of the electronic display device 1802 when the electronic display device 1802 may be in a vertical position. Further, when the electronic display device 1802 may be tilted counterclockwise up to 90-degrees, the output indicating device 1800 may end up in the left upper corner of the electronic display device 1802.

Figure 19:
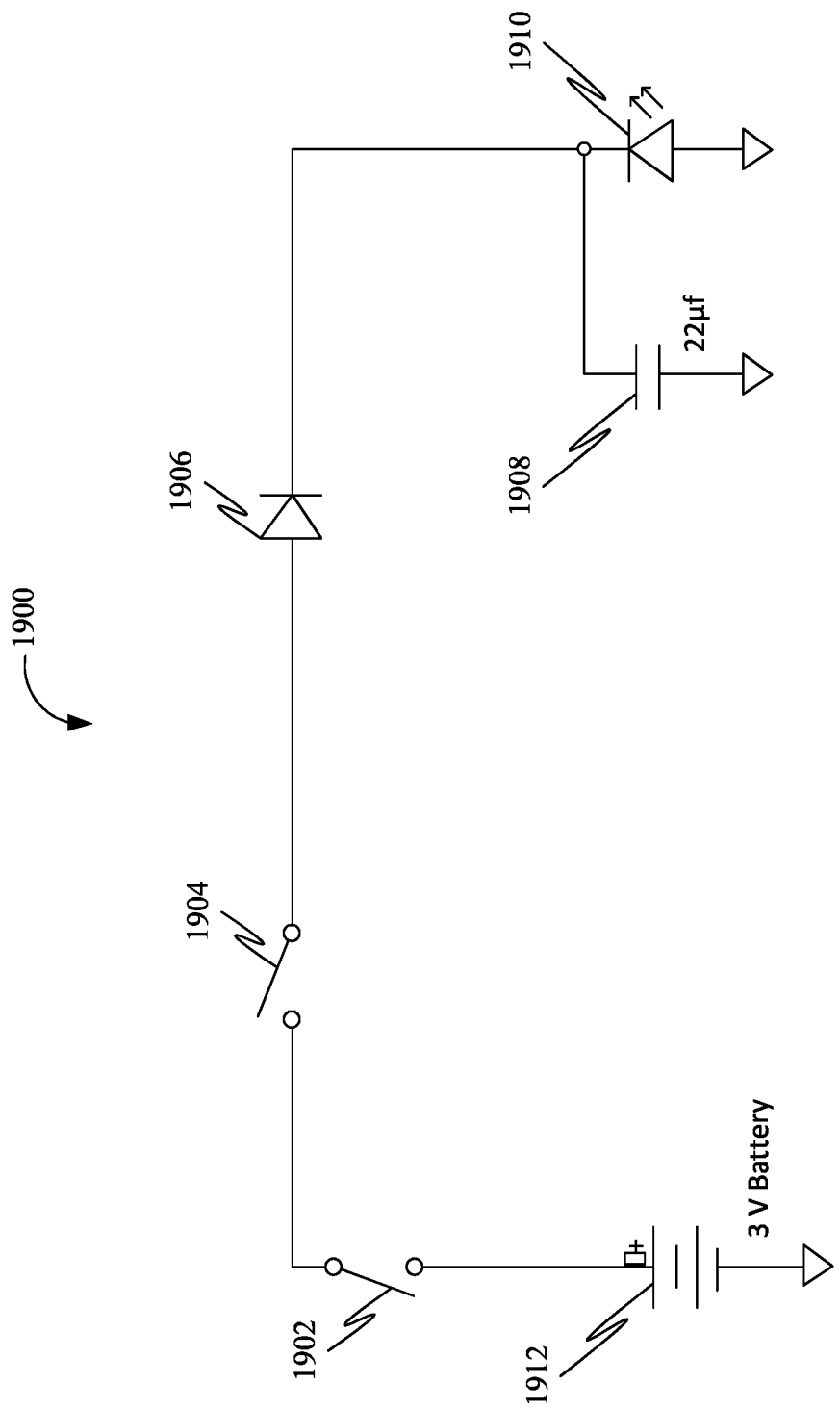
FIG. 19 is an electrical circuit for a system for measuring the orientation of an electronic display device to aid in the correction of a viewing position of a user, in accordance with some embodiments.

FIG. 19 is an electrical circuit 1900 for a system for measuring the orientation of an electronic display device to aid in the correction of a viewing position of a user, in accordance with some embodiments. In some embodiments, the system may include a switch 1902 on Y-axis (60-degree switch on Y-axis), a switch 1904 on X-axis (60-degree switch on X-axis), a blocking diode 1906, a leveling capacitor 1908, a light-emitting diode (LED) 1910, and a 3V battery 1912. Further, in an instance, the switch 1902 may be turned on when the electronic display device may be tilted up to 60-degrees in a vertical direction. Further, in an instance, the switch 1904 may be turned on when the electronic display device may be tilted up to 60-degrees in a horizontal direction. Further, the blocking diode 1906 may prevent the flow of reverse current in the electrical circuit 1900. In an instance, the system may include the leveling capacitor 1908 to detect the inclination and tilt of the electronic display device. Further, the system may include the LED 1910 as the output indicating device. In an instance, when the electronic device may be tilted 60-degrees in either vertical direction or horizontal direction, the LED 1910 may turn on. In an instance, the system may include the 3V battery 1912 as a power source. In some embodiments, the power source may include a solar power source.

Figure 20:
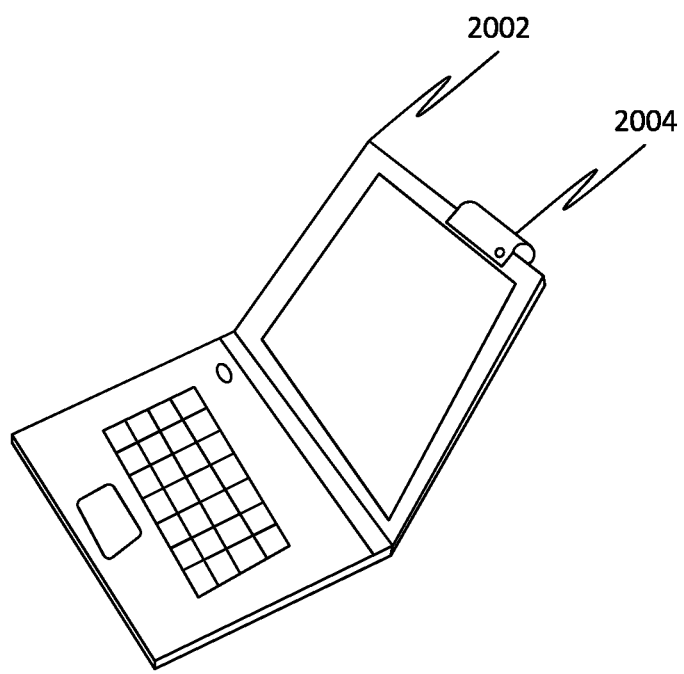
FIG. 20 is an exemplary representation of a system for measuring the orientation of an electronic display device to aid in the correction of a viewing position of a user, in accordance with some embodiments.

FIG. 20 is an exemplary representation of a system for measuring the orientation of an electronic display device 2002 to aid in the correction of a viewing position of a user, in accordance with some embodiments. In some embodiments, the system may be configured to be attached or detached from the electronic display device 2002, such as through a dedicated mechanism 2004. The dedicated mechanism 2004 may allow the system to attach to the electronic display device 2002 to determine correct tilt angle. Further, the system may also be integrated into other cases that may be used for PDA's such as a Kindle™ reading cases or IPad™ cases, etc. The system may also be placed into other cell phone cases that may have other graphic designs. This would allow a person to keep the system and transfer it to other designed cases for use with their existing electronics thus reducing cost and increasing variety and personalization.

Figure 21:
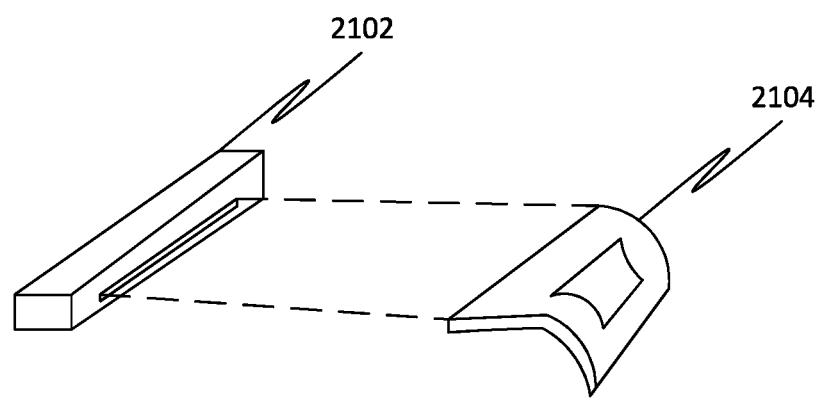
FIG. 21 is an exemplary representation of a hook, in accordance with some embodiments.

Further, the dedicated mechanism 2004 may include a metal piece 2102 and a magnet 2104 forming a hook shown in FIG. 21. All electronics including battery, motion on/off motion switch, inclinometer switches, biofeedback (LED, Vibration, sound), micro USB, and memory board may be contained in the metal piece 2102. This metal piece 2102 once detached can be attached to the magnet 2104 (the hook) via metal-magnet integration.

In an instance, the system may be placed in on the top of the electronic display device 2002. In some embodiments, the electronic display device 2002 may include, but may not be limited to, a laptop, a phone, an electronic reading device, and so on. Further, in some embodiments, the system may measure the orientation of an electronic display device 2002, such as a laptop when a user may use the laptop. In an instance, the screen of the laptop may be in a more stretched position when a user may not be using the laptop in a correct angle of viewing. Further, the screen of the laptop may be in a less inclined when the user may be using the laptop in a correct angle of viewing. In an instance, the hook may easily be removed from the electronic display device 2002 once the work may be finished. In some embodiments, the system may allow determining a correct tilt angle of the electronic display device 2002.

Figure 22:
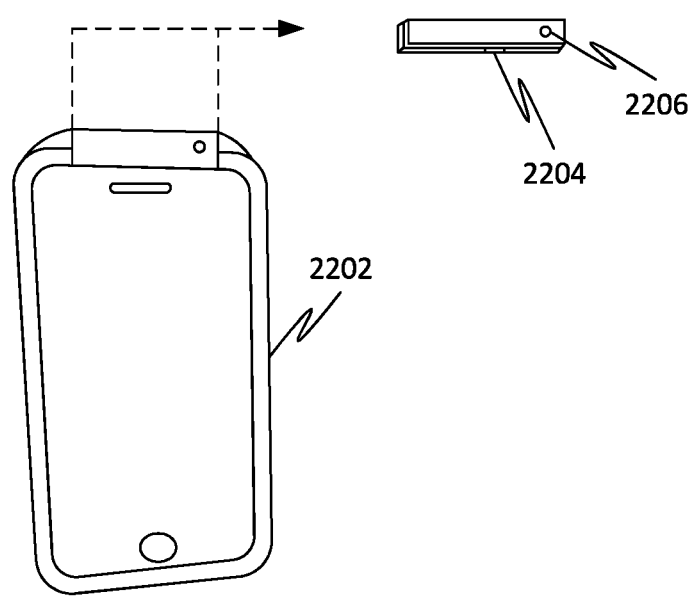
FIG. 22 is an exemplary representation of the system to be attached to an electronic display device, in accordance with some embodiments.

In some embodiments, the system may be configured to communicate with an electronic display device 2202, such as a smartphone, a laptop, a tablet, and so on using wired connection such as micro-USB 2204 (shown in FIG. 22), USB-C, a lightning connector, and so on, and transmit the sensory data. Further, in an instance, the system may be configured to be electrically powered by the electronic display device 2202, or an external power source, such as through the wired connection including micro-USB, USB-C, a lightning connector, and so on. Further, the system may include an LED 2206 to provide an indication to a user.

Figure 23:
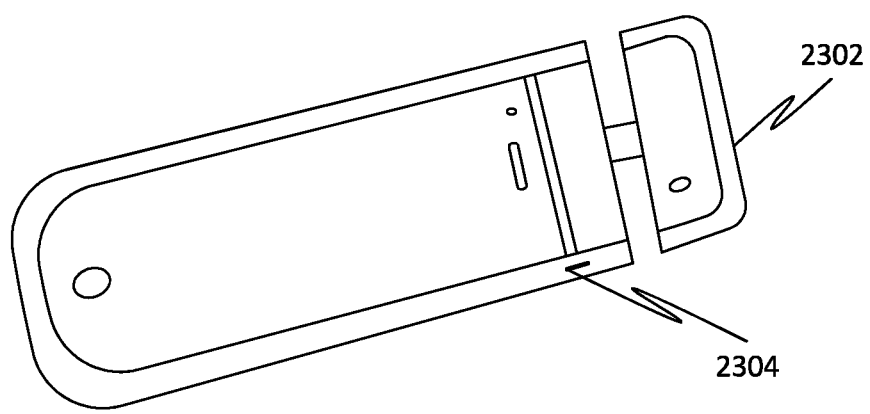
FIG. 23 is an exemplary representation of a system for measuring the orientation of an electronic display device to aid in the correction of a viewing position of a user, in accordance with some embodiments.

FIG. 23 is an exemplary representation of a system for measuring the orientation of an electronic display device to aid in the correction of a viewing position of a user, in accordance with some embodiments. Further, the system may be configured to be attached or detached from the electronic display device, such as through a dedicated mechanism. Further, the dedicated mechanism may include a clip acting as a hook. Further, the plastic clip may be attached or detached from the electronic display device. Further, the plastic clip may fit on the top of the electronic display device and may attach the system to the electronic display device.

Figure 24:
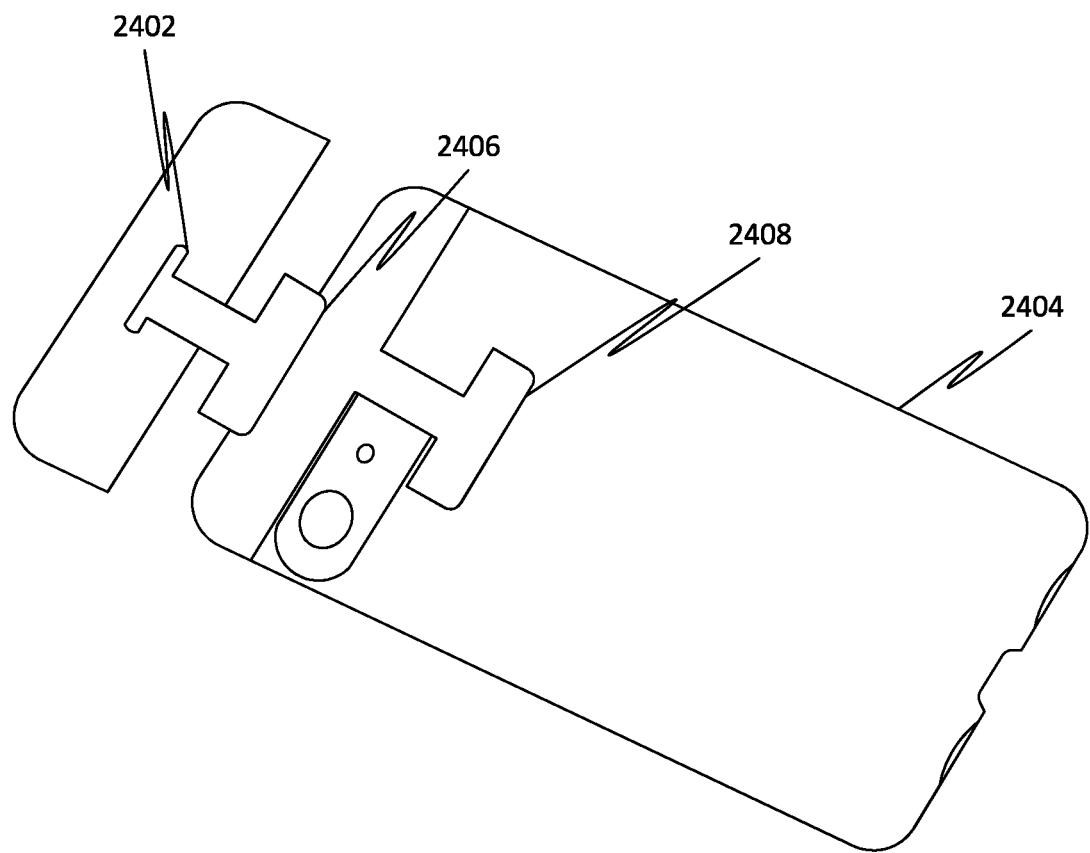
FIG. 24 shows an embedded plastic hinge that fits into the plastic phone mold/case, in accordance with some embodiments.
Figure 25:
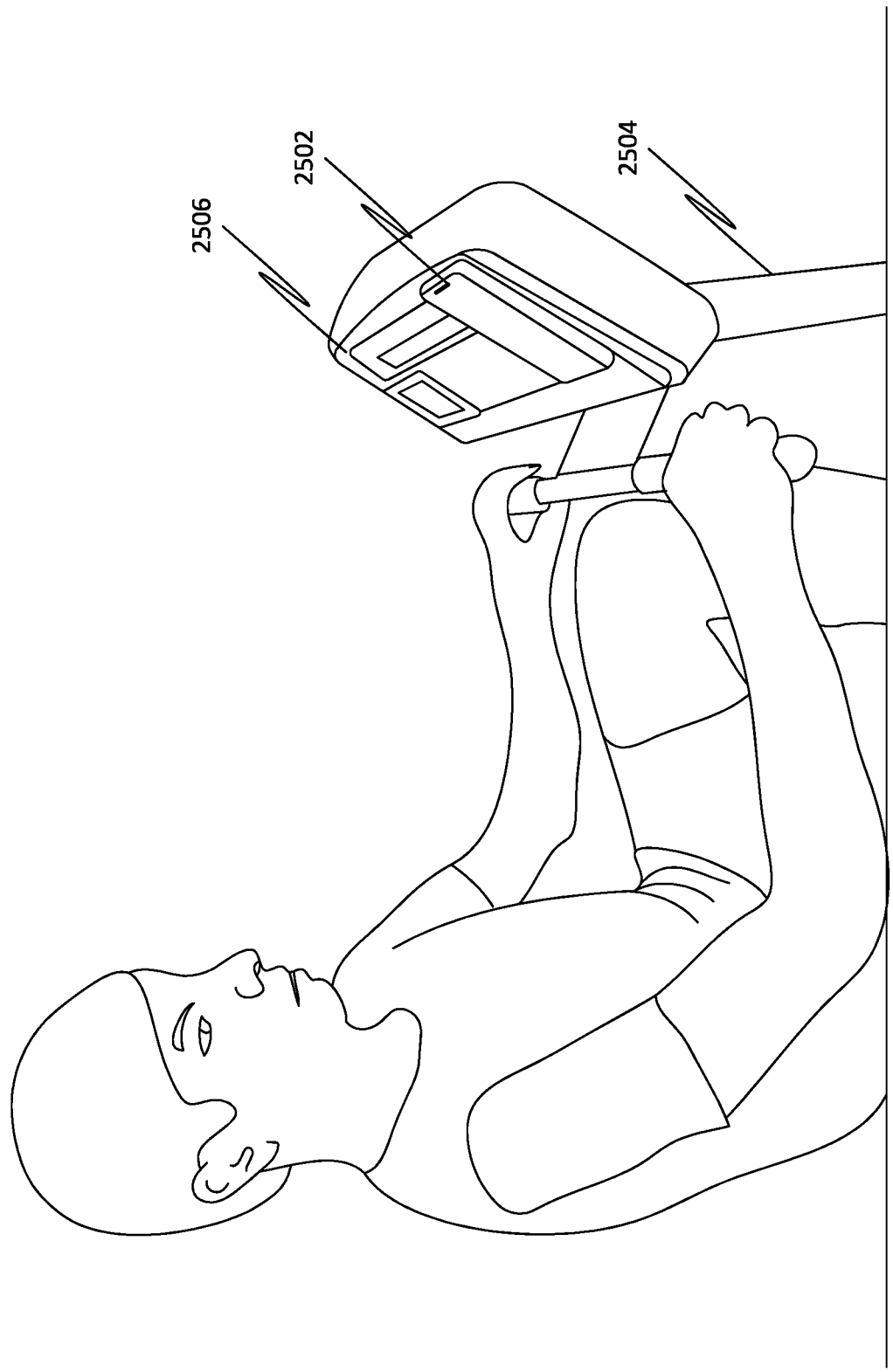
FIG. 25 shows an electronic device affixed to an exercise equipment, in accordance with some embodiments.
Figure 26:
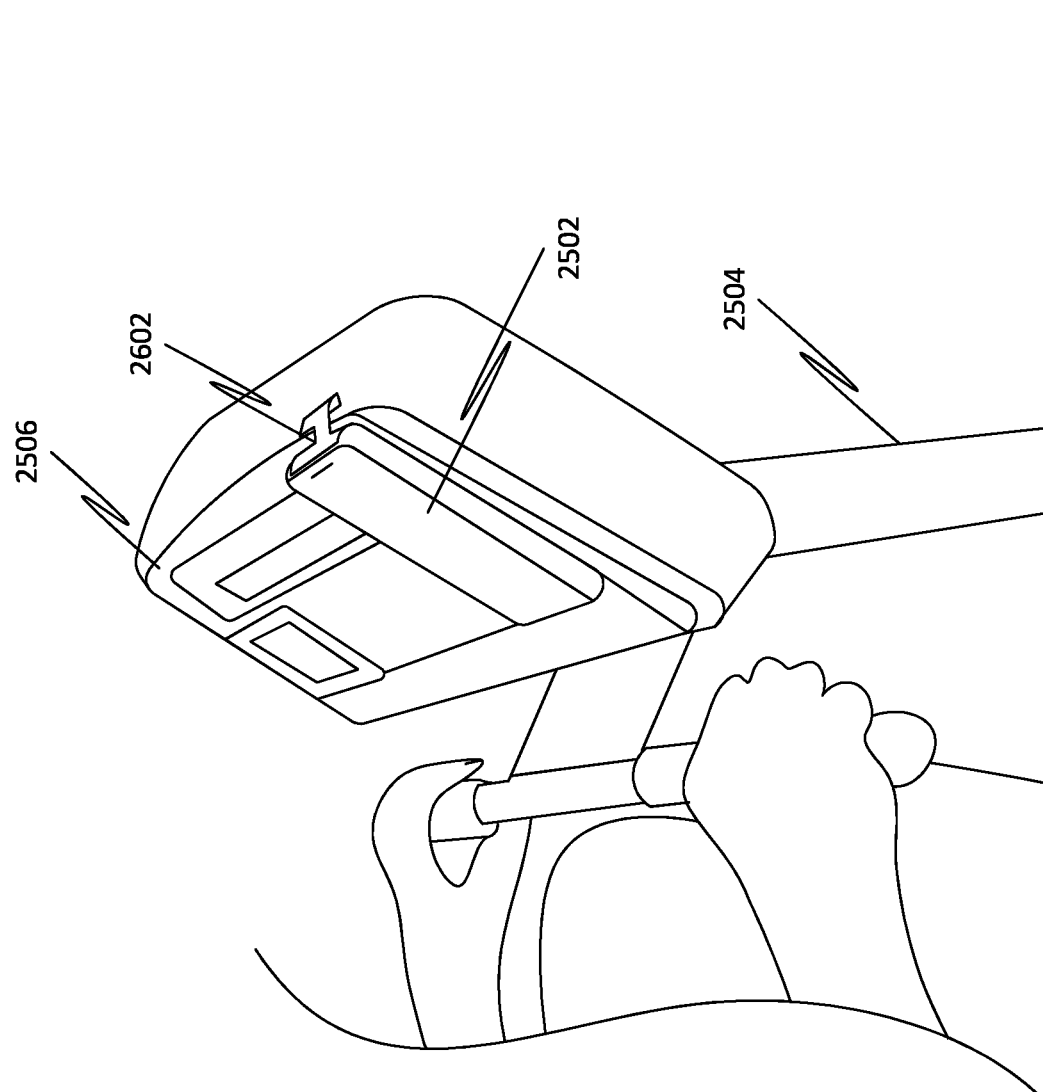
FIG. 26 shows a partial close-up view of an electronic device affixed to an exercise equipment, in accordance with some embodiments.

The electronic device 2302 may be removable with plastic clips 2304. It may contain an embedded plastic hinge 2402 that fits into the plastic phone mold/case 2404 as shown in FIG. 24. It will contain a hinge that stops at 90 degrees. The embedded plastic hinge 2402 will be useful to attach the electronic device to a laptop or other viewing device. A hook catch 2406 may also allow for placement of the entire phone on top of a viewing screen such as a laptop to set the angle of the screen. A pocket clip 2408 may be used to attach the electronic display device in a pocket. It may also be used to affix the electronic device 2502 to other viewing screens such as exercise equipment 2504 (such as a treadmill, Gym-bike, elliptical or any equipment) that has a viewing position, as shown in FIGS. 25-26. This will allow for a better angle of the neck while using the exercise equipment 2504. Further, the electronic device 2502 may be placed on a display device 2506 of the exercise equipment 2504. In some embodiments, the system may be attached to the exercise equipment 2504 through a hook 2602. FIG. 26 is a close-up view for an exemplary representation of a system for measuring the orientation of an electronic display device 2506 to aid in the correction of a viewing position of a user, in accordance with some embodiments.

Further, the disclosed system not only gives direct biofeedback for immediate correction but it also allows a learning process to occur over time.

The system may include a micro-USB connection that may allow for the charging of the internal lithium battery. Further, the micro-USB may also allow for data analysis.

The system may be turned on via a micro-motion switch or inclinometer switch set at 10-30 degrees and will turn off after the switch has allowed for 10 seconds of biofeedback unless the 70-85 degree inclinometer switch shuts the biofeedback mechanisms off first. This is important due to the fact that most people place their phones on a tables/seats or flat surfaces and the device would continue to produce biofeedback when the phone is not in use without this function. The intent is to decrease annoyance and increase battery life.

Once the system has been turned on via movement and it is positioned to turn off the inclinometer switch it would indicate that the device is in use and enter a data point for later computer analysis.

The data collected could be analyzed via a computer program or application. The data collected could be used to see how the person is responding to the biofeedback device when it is on or off.

When a person turns the biofeedback signal off via computer program it will continue to enter data as it relates to the movement of the inclinometer switches.

This data will allow for the person to see if their behavior or positioning of their neck/back has improved. This is explained further in conjunction with FIGS. 27-29 below.

For example: If the person used the device for one week and then turned the Biofeedback signal off for one week an analysis may show that their compliance is not within a corrective goal. Therefore, the advice may be to continue using the biofeedback signal for an additional 3 weeks in order to increase compliance.

Figure 27:
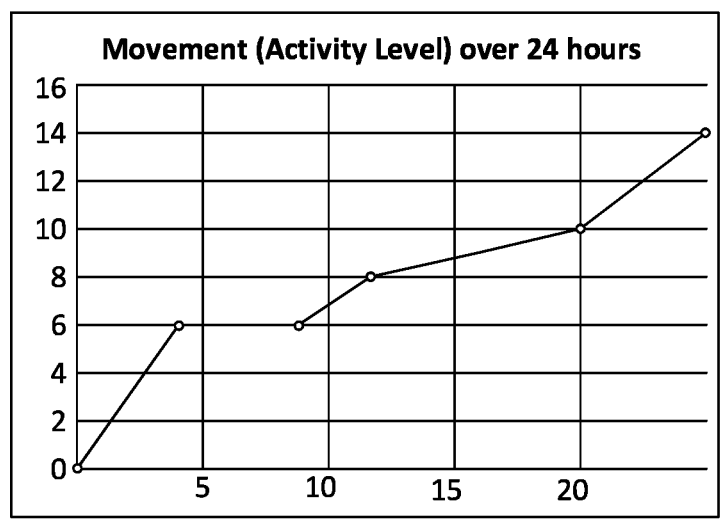
FIG. 27 is a visualizations generated by the system for measuring the orientation of an electronic display device to aid in the correction of a viewing position of a user, in accordance with some embodiments.
Figure 28:
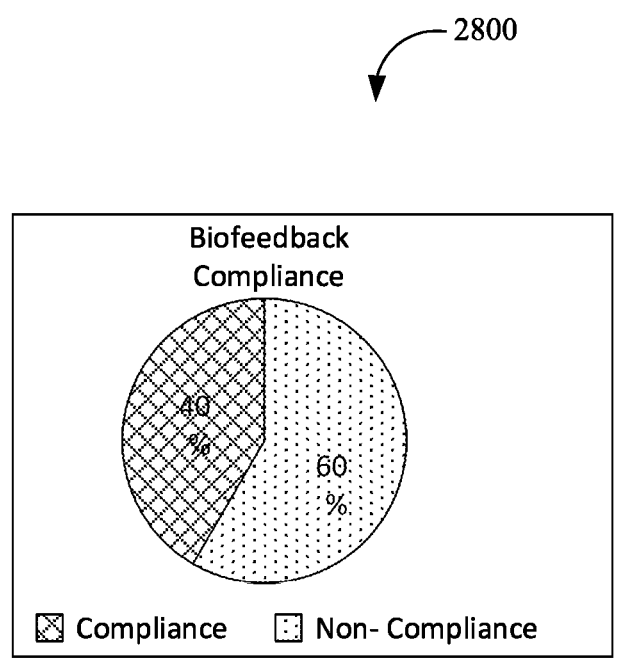
FIG. 28 is a visualizations generated by the system for measuring the orientation of an electronic display device to aid in the correction of a viewing position of a user, in accordance with some embodiments.
Figure 29:
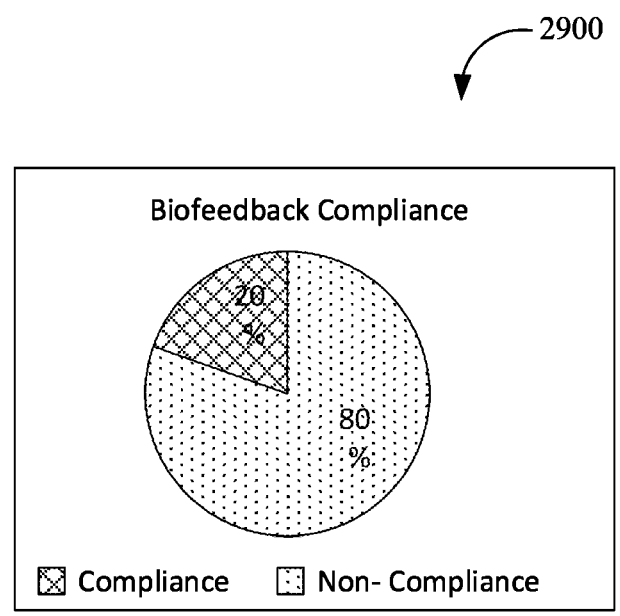
FIG. 29 is a visualizations generated by the system for measuring the orientation of an electronic display device to aid in the correction of a viewing position of a user, in accordance with some embodiments.

FIGS. 27-29 represents various visualizations 2700-2900 generated by the system for measuring the orientation of an electronic display device to aid in the correction of a viewing position of a user, in accordance with some embodiments. In some embodiments, the sensory data may be analyzed and visualizations 2700-2900 may be generated. Further, the visualizations 2700-2900 may provide in-depth details about the posture of the user while operating the electronic device. In an instance, the analytics generated may determine the behavior or positioning of the neck of a user. Further, the analytics generated may allow the user to improve their posture of the neck as a corrective goal.

Further, the disclosed system may also help to reduce injuries that have been on the rise with people running into objects/automobiles from looking in a downward position while using their phones or PDAs. Many accidents are being reported about people being hit by cars due to the fact that they are fixated in a downward-looking view. The system may raise the phone and increase the peripheral view which may reduce the rate of accidents. For example, New York is in the process of making it illegal to cross the street while using a cell phone due to people getting struck by motor vehicles.

Figure 30:
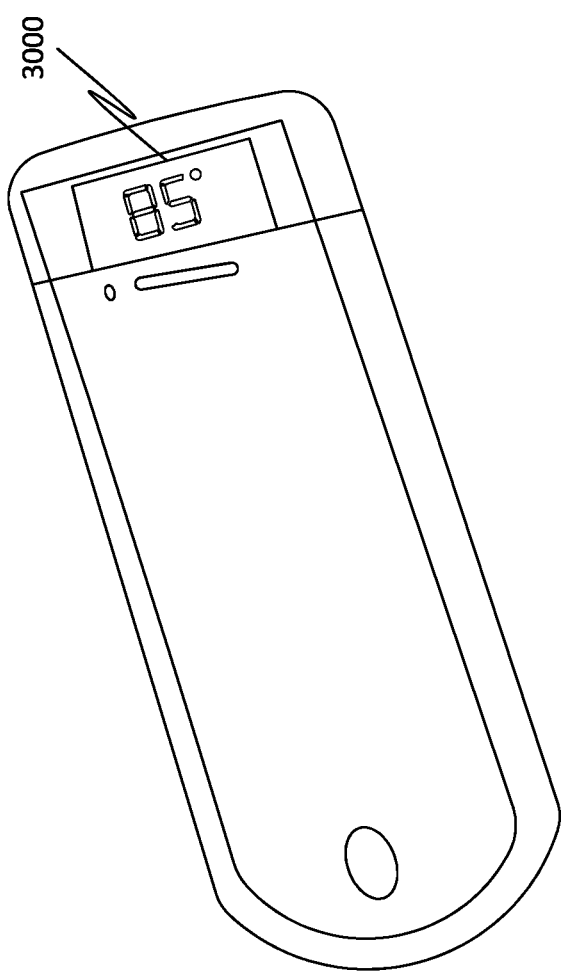
FIG. 30 is an exemplary representation of a system for measuring the orientation of an electronic display device to aid in the correction of a viewing position of a user, in accordance with some embodiments.

FIG. 30 is an exemplary representation of a system for measuring the orientation of an electronic display device to aid in the correction of a viewing position of a user, in accordance with some embodiments. In some embodiments, the system may also be placed on the electronic display device such as, but may not be limited to, a digital real-time temperature gauge 3000. In some embodiments, an external device may be used to provide information about the posture of a user to the electronic display device. In an instance, the external device may include a measuring device. Further, the measuring device may include a tilt switch or a strain gauge to determine a forward bent of the user. In some embodiments, the external device may be placed on the body of the user. In an instance, the external device may be placed on the lower cervical spine or on at the Lumbar spine of the user. Further, in an instance, the external device may affix to the skin of the user by a mean such as, but not limited to, an adhesive tape, a waist belt, a belt clip, and so on.

Further, in an embodiment, the external device may communicate with electronic display devices over a communication network such as, but may not be limited to, a Bluetooth, a Wi-Fi, and so on.

In some embodiments, the system for measuring the orientation of an electronic display device to aid in the correction of a viewing position of a user may include a shock-absorbing device. Further, the shock-absorbing device may include a polyurethane material with a visco-elastic property. In an instance, the visco-elastic property may allow the device to act as a liquid to absorb shock and as an elastic solid when kept at rest. Further, in some embodiments, the system may be waterproofed. In an instance, the system may be rated with IP68 which may allow the protection of the system in water up to a depth of 1.5 meters.

According to some embodiments, the top part of a case that contains a biofeedback electronic device can be removed and replaced with an accessory that cell phones or PDA cannot provide. This may include the digital real-time temperature gauge 3300 which may have other functions such as humidity or altimeter. These accessories could be designed to fit into the contour of the replaced Biofeedback electronics device. An accessory that may be developed to replace the electronic device may be a slide on a piece that completes the case without any electronic device contained.

The disclosed system may be incorporated into a smart phone or PDA mobile device. The incorporation of this technology may be programmed into a smartphone or PDA device. The programming of the phone/PDA would use its internal inclinometers to set the angle of Biofeedback to elicit a response of LED, vibration, or sound with the addition of allowing the phone screen to turn off or illuminate at a specific angle to influence the user to change viewing position for an anatomical favorable position.

Further, the inclinometer may include, but not limited to, gravitational sensors, accelerometers, conductive inclinations sensors, Microelectromechanical systems, or gyroscopes for use of measuring phone viewing angles.

Figure 31:
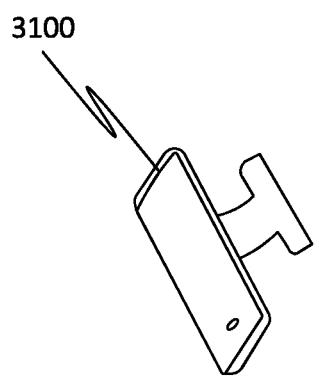
FIG. 31 is an exemplary representation of a system for measuring the orientation of a conventional book to aid in the correction of a viewing position of a reader, in accordance with some embodiments.

FIG. 31 is an exemplary representation of a system 3100 for measuring the orientation of a conventional book to aid in the correction of a viewing position of a reader, in accordance with some embodiments. An electronic device when removed from a case of the system 3100, will not only allow for laptop corrections but it can be used to help people with correct positioning while reading a book. Further, in some embodiments, the system 3100 may include a sensory device and an output indication device. Further, the sensory device may include an inclinometer sensor switch configured to sense the inclination of the conventional book from a horizontal level. Further, the output indication device may include a device such as, but not limited to, an LED, a haptic motor for vibration, a beep sound generating device, and so on. Further, in an instance, the output indication device such as an LED may turn on when the reader reads the conventional book in an incorrect position. Further, the incorrect position may include a horizontal position or a less inclined position which may lead to spinal disc pressure as well as increased musculoskeletal stress. Further, the LED may turn off when the reader reads the conventional book in a correct position, Further, the correct position may include an inclination of the conventional book to an angle such as, but not limited to, 60 degrees, 70 degrees, 80 degrees, or 90 degrees. The correct angle of inclination may change from 0 degrees to 90 degrees according to the convenience of the reader.

Figure 32:
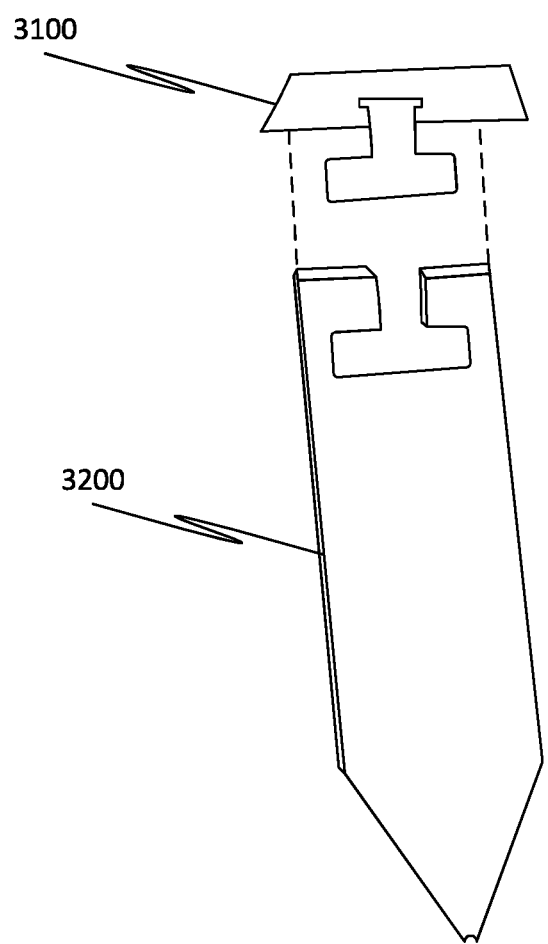
FIG. 32 is an exemplary representation of the system attached or inserted to the top of a plastic bookmarker, in accordance with some embodiments.
Figure 33:
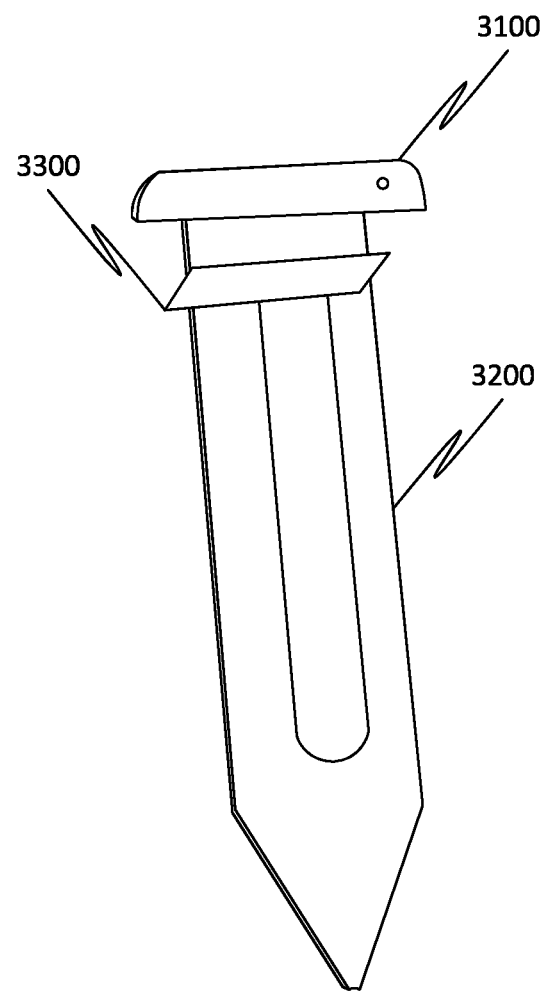
FIG. 33 is an exemplary representation of the system attached or inserted to the top of a plastic bookmarker, in accordance with some embodiments.
Figure 34:
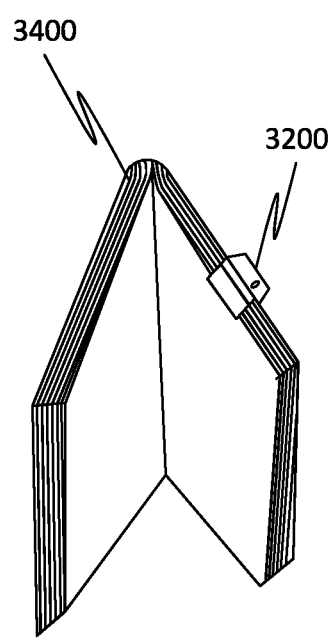
FIG. 34 is an exemplary representation of a plastic bookmarker placed in the back of a conventional book, in accordance with some embodiments.

Further, in some embodiments, the system 3100 may be attached or inserted to the top of a plastic bookmarker 3200 as shown in FIGS. 32-33. Further, the plastic bookmarker 3200 may include a clip configured to place the plastic bookmarker 3200 in the back of a conventional book 3400 as shown in FIG. 34. Further, the plastic bookmarker 3200 may include a ledge 3300 configured to rest at the top of the pages of the conventional book 3400. Further, the system 3100 may be attached above the ledge 3300 to measure the inclination of the conventional book 3400. Further, in some embodiments, the ledge 3300 may contain an LED light for reading.

Figure 35:
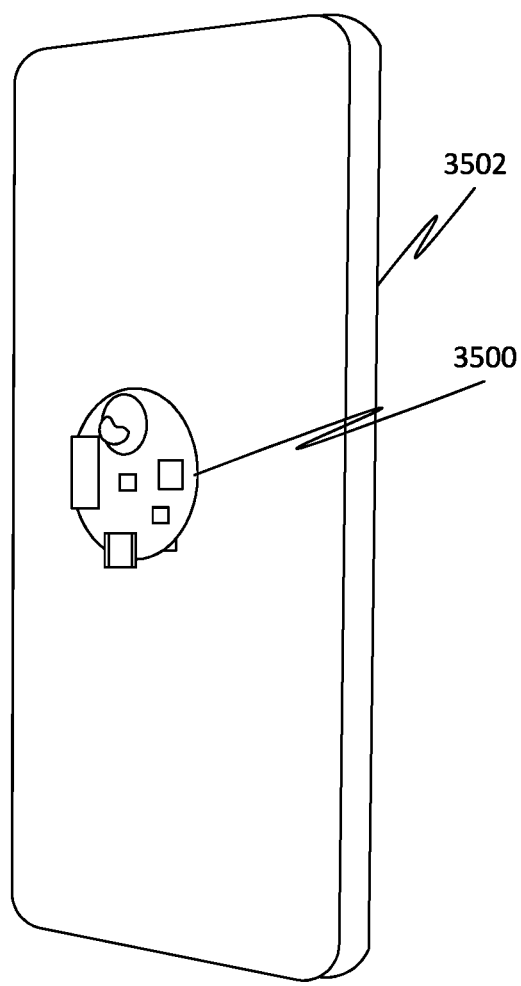
FIG. 35 is an exemplary representation of an external device placed on a smart phone, in accordance with some embodiments.

FIG. 35 is an exemplary representation of an external device 3500 placed on a smartphone 3502, in accordance with some embodiments. Alternatively, the external device 3500 may be placed on other electronic communication devices such as PDAs. Alternatively, the external device 3500 may be placed within an electronic communication device.

Further, the external device 3500 may be easier to produce without making multiple cases at this time and will fit on just about any phone or PDA. The vibration will be provided as the primary source of Biofeedback.

The external device 3500 is configured to correct posture by way of the smartphone 3502 positioning so that the viewing screen influences the user to raise their neck into the correct position avoiding prolong flexion or forward bending of the neck. Further, the external device 3500 may operate in conjunction with an application. This application works with the external device 3500 in Portrait and Landscape use.

Further, the external device 3500 may include a touch sensor that will place around the external device 3500 so that it will likely be touch when in use. This will reduce false positives that might be detected, when people may place their phone or PDA on a stand or possible in a pocket or backpack etc. Without the touch sensor, the external device 3500 would pick up the movement and provide date as if it were actively being used (false positive). Further, the external device 3500 may include thermal sensors too to reduce false positives.

Figure 36:
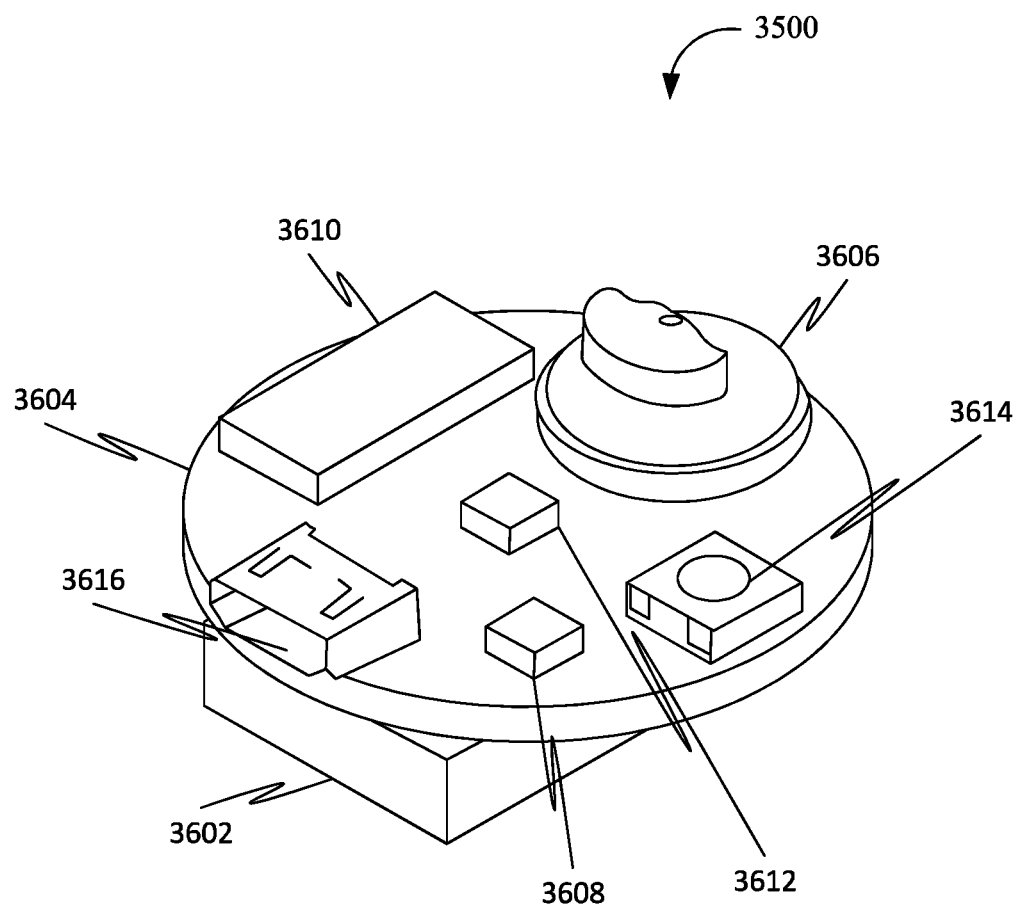
FIG. 36 is an exemplary representation of the external device, in accordance with some embodiments.

FIG. 36 is an exemplary representation of the external device 3500, in accordance with some embodiments. The external device 3500 may include an accelerometer 3612 and a LiPo battery 3602 placed on a PCB board 3604. Further, the external device 3500 may include a vibration motor 3606, a LED light 3608, and a Bluetooth module 3610. Further, the external device 3500 may have a plastic clamshell that encloses it. It may also have a soft shell that may be used for various designs or licensing logos etc. The entire external device 3500 may be placed and affixed to the back of the cell phone or PDA as shown in FIG. 35. Further, a touch sensor may be placed in a strategic way on the larger PDA devices so that the user is likely to touch the strips while the PDA is in use (such as along the sides of the PDA). Further, the external device 3500 may include a push-button 3614 and a mini-USB port 3616. Further, the external device 3500 may be named "SwivX".

Figure 37:
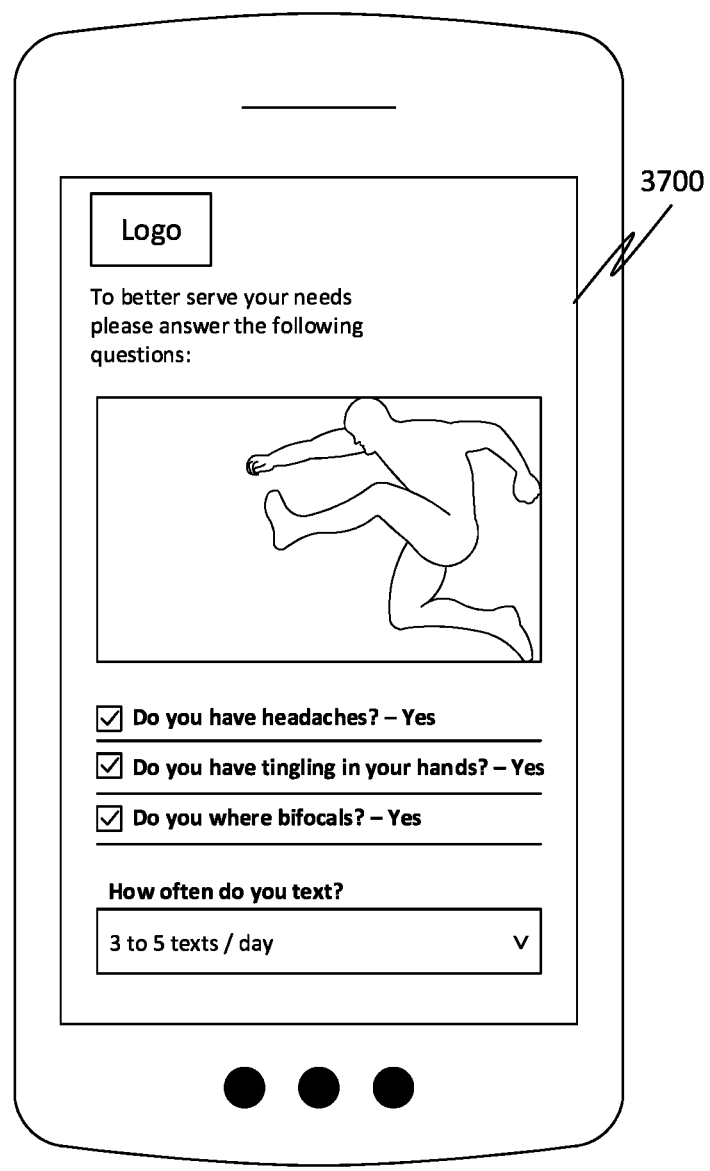
FIG. 37 is an exemplary user interface of an application in accordance with exemplary embodiments.
Figure 38:
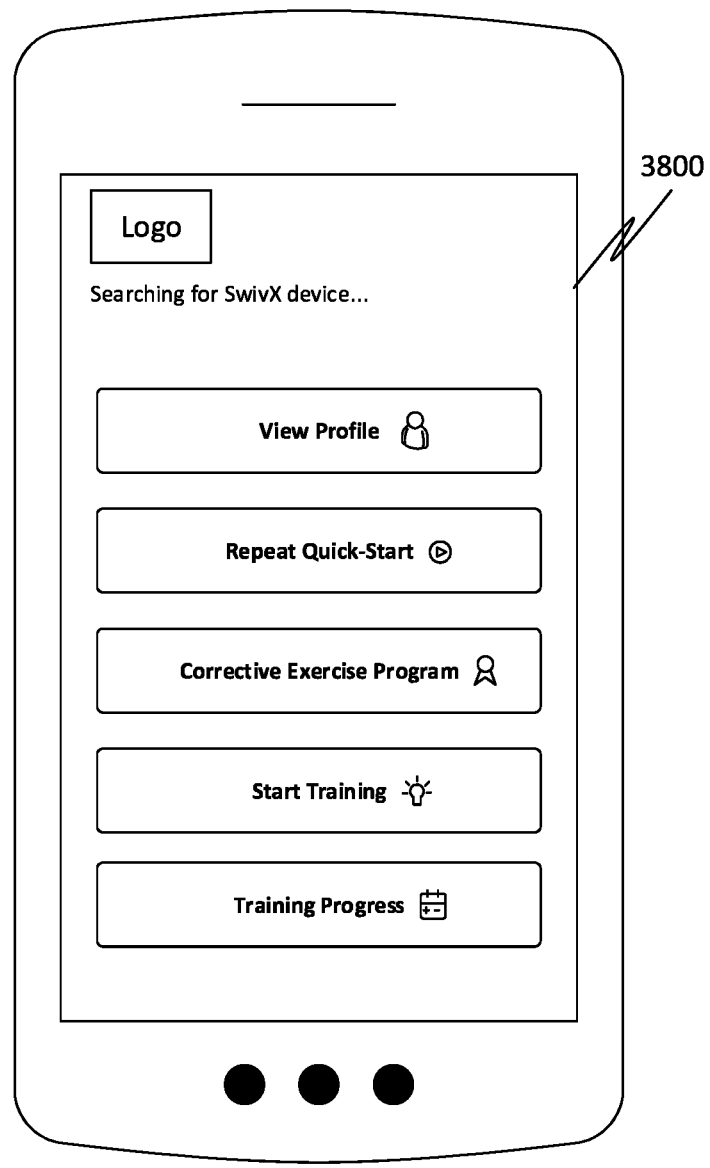
FIG. 38 is an exemplary user interface of the application in accordance with exemplary embodiments.

In accordance with some embodiments, an application is disclosed. FIGS. 37-40 are user interfaces 3700-4000 of the application in accordance with exemplary embodiments. Along with the external device 3500, the user will be provided instructions on placement and affixing the external device 3500 to the phone. The external device 3500 will also serve as a grip holder that is designed to fit the contour of the fingers which will enhance to the ability to hold the phone in the correct position. Once the external device 3500 is affixed they will be instructed to download the application. After the application is launched, it may ask a series of questions (as shown in FIG. 37) and a disclaimer agreement. As shown in FIG. 38, the application may allow the user to access the user profile, repeat a quick start, corrective exercise program, start training, and track training progress. There may be a quick start program that has default settings and a training mode. The training mode may ask several questions including pain level and areas of pain. Further, 4 different outcomes may be present when the user enters their information.

1. Angle of activation
2. Strength of vibration.
3. Pulse frequency of Vibration
4. Time delay of Vibration.

If for a person, the application shows data that would represent severity of pain that is high and older age and location for disc-related symptoms, then the person training may be placed into a stricter or rigid format. The angle may be steep 85 degrees with a quick strong pulse and 0 to 0.5-sec delay. In contrast, if a user was not in significant pain as per data entered and they are under 30 years old with a location of pain that does not represent disco-genic pathology then their external device 3500 may function with a light vibration and long pulse frequency. The angle may be less steep at say 65 degrees and the delay may be a 3 sec before vibration is activated. All 4 device outcomes can be manually overridden so that the user can customize the device to their desire. The application training also has a special feature called percentage compliance training. It allows the user to use the external device 3500 without vibration or Biofeedback for a 24-hr time while it continues to collect data. It then turns the vibration on for 24 hours and shows by way of graphs (as shown in FIGS. 27-29) and statistical analysis how much improvement was made or percentage improvement. It may then shut off the vibration for 24 hours again. The calculated measure may show how much the user's behavior has changed. This has been termed percentage compliance.

Figure 39:
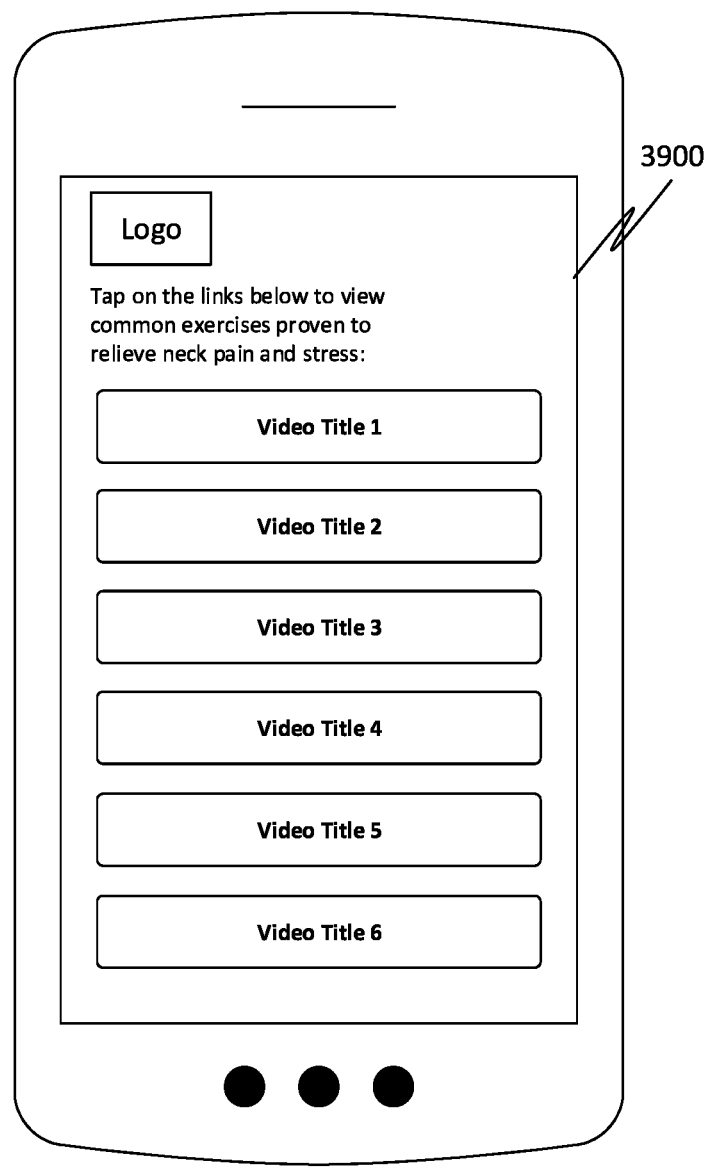
FIG. 39 is an exemplary user interface of the application in accordance with exemplary embodiments.
Figure 40:
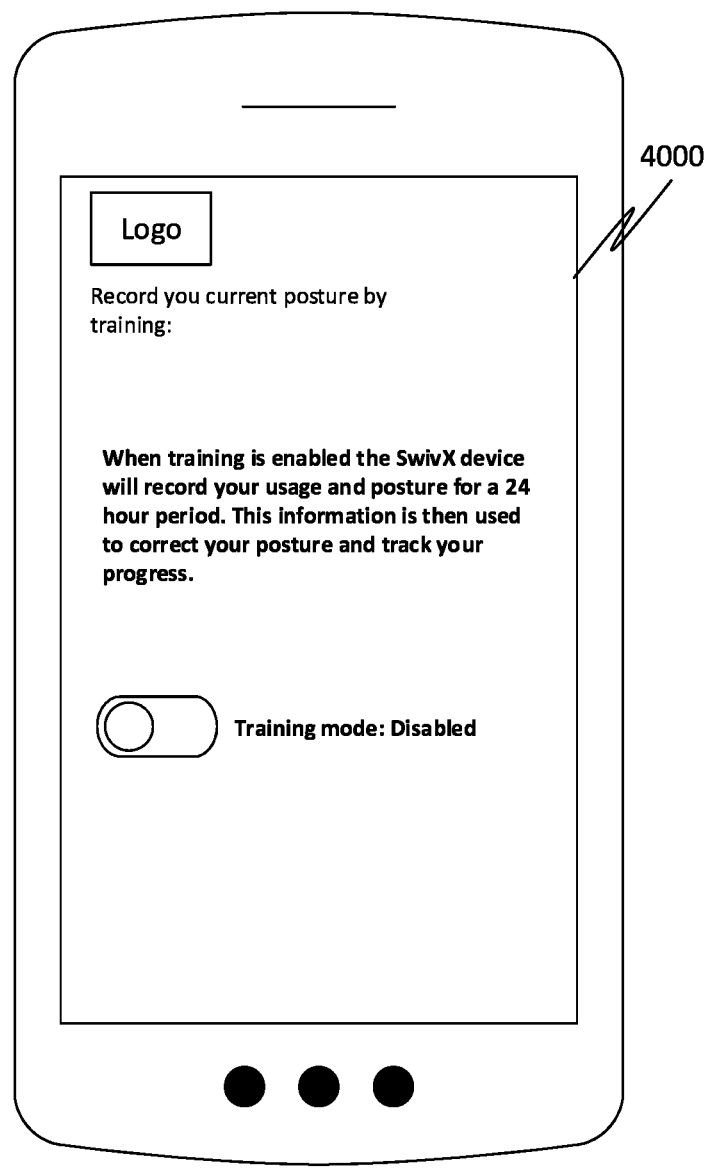
FIG. 40 is an exemplary user interface of the application in accordance with exemplary embodiments.
Figure 41:
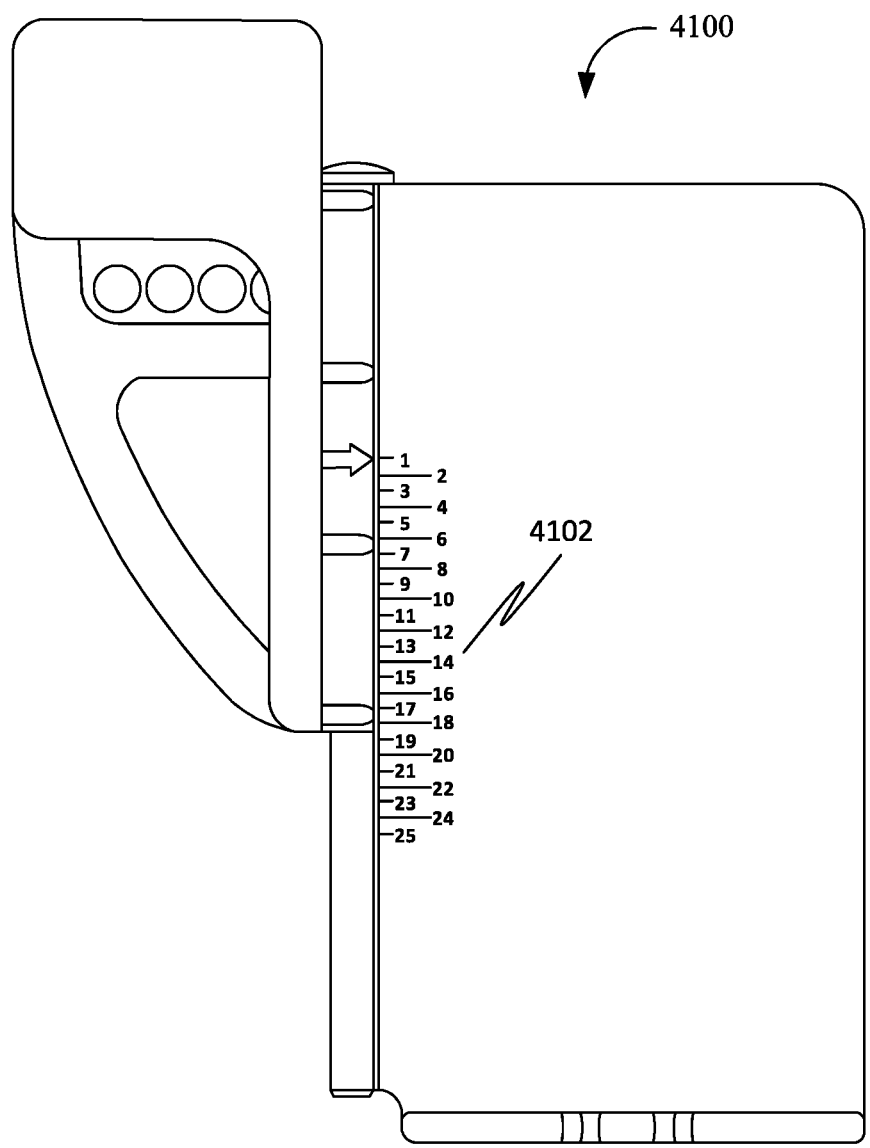
FIG. 41 is a front view of a bracket, in accordance with some embodiments.
Figure 42:
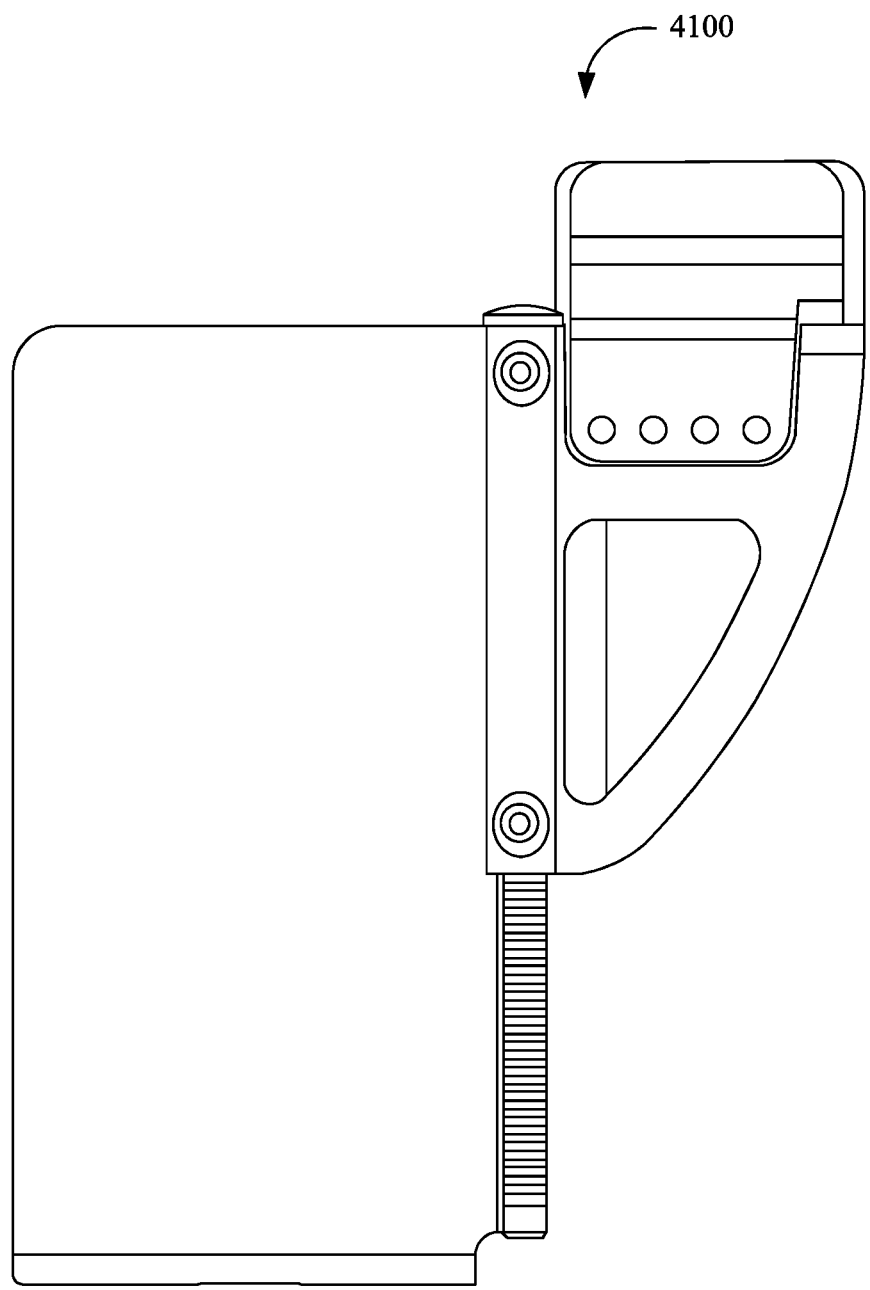
FIG. 42 is a back view of a bracket, in accordance with some embodiments.
Figure 43:
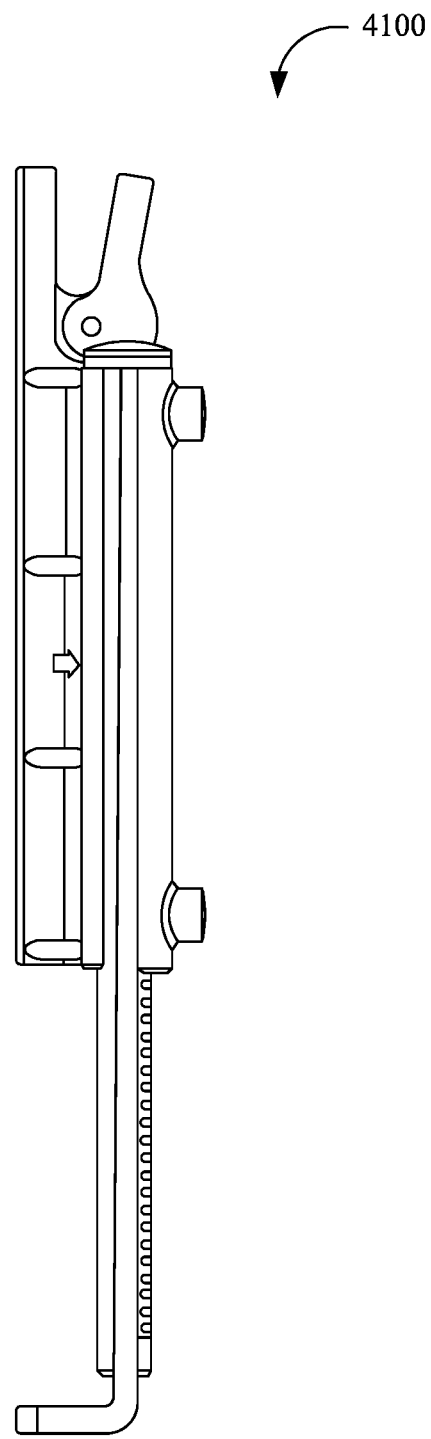
FIG. 43 is a side view of a bracket, in accordance with some embodiments.
Figure 44:
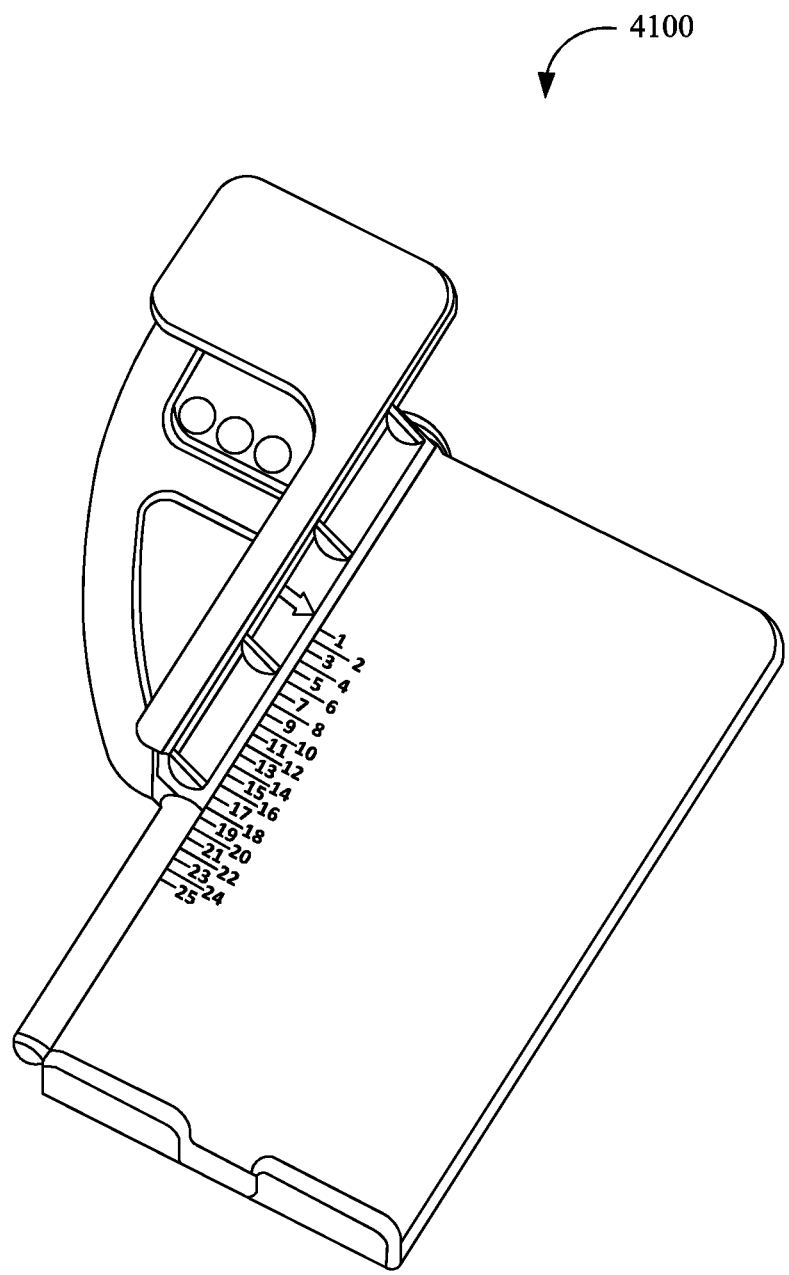
FIG. 44 is a perspective view of a bracket, in accordance with some embodiments.

Further, the user may have the ability to choose from corrective exercises that are linked to Google™ etc. The user may also have the ability to choose links to instructional videos as shown in FIG. 39. The application may also provide analytical information to be shown in graphs. This data may show how long and how often a user is in various positions. It may have a real-time active mode which shows the angle of the phone or PDA and how it correlates to the anatomical position of the neck and spine. As shown in FIG. 40, the application may allow the user to enable or disable training.

FIGS. 41-44 show various views of a bracket 4100, in accordance with some embodiments. The bracket 4100 may mount on the right side of practically any electronic communication device such as a laptop computer or a smartphone. The bracket 4100 may have special calibration numbers 4102 that allows for all phones to be calibrated to the external device.

Further, the application may direct the user to take a selfie with the arms straight out in a horizontal position. The application may then direct the user to place their phone on the bracket 4100 located at the right side of the computer and sets the bracket calibration for their phone. The application program may give the user a step by step procedure to set their placement of a chair correctly and by way of the accelerometer on the external device, it may show the user, the correct tilt angle of the computer screen for viewing. Once this is set, the application may direct the person by way of facial recognition programming to move their electronic communication device to and fro (axis x, y), as well as, elevation (z) to the correct height for optimal ergonomic with the eye looking at the top half of the computer viewing screen. This is accomplished by calculation from the initial selfie set point of reference. Once the user has accomplished the procedure correctly, a certificate may be printed or sent by way of an email. The parameters of all the settings may be adjusted manually. The application has to ability to be set for a sit-stand work station. If the user sets the device in a sitting position, the data will be stored, and then additionally they set the device in the standing position and both data points will be stored. The user may be able to toggle back and forth from sitting to standing and the external device may calibrate to their last setting so that they do not have to repeat the setup process over and over. Additionally, the user may have the ability to set an alarm on the application which instructs the user to do specific exercises/stretches every 15 minutes on a reoccurring interval. This may be set to the desire of the user up to 3 hr for reoccurring intervals.

In some embodiments, an ergonomics step process is disclosed. First, a user takes a selfie with arms horizontal to the floor and places a pillow at the lower back to support the arch. Second, the user places the phone on the monitor bracket (such as the bracket 4100). Then the user places top of the smartphone level to monitor. Then, the user enters the calibrated number that the arrow is pointing to (in the application). Third, the user adjusts the seat height to set the correct work desk height by placing a bent arm to the side with an elbow at the midline. Fourth, the user places three fingers starting at the tip of the elbow. The first of the three fingers should be level to the desktop. Fifth, the user enters the start interactive placement on application. The user may place their electronic communication device (such as a laptop) via application instructions for their electronic communication device (such as a laptop) placement. This uses facial recognition for height and distance. The tilt of the monitor may be determined by the device accelerometer. The application may automatically determine and guide the user to determine the best placement of the electronic communication device (such as a laptop) for height and distance. This may require an external keyboard and a stand (object) to be placed under the electronic communication device (such as a laptop). Sixth, the user is set up to the correct ergonomic. So, a certificate of completion may be emailed According to some embodiments, ergonomic steps with a combination of accelerometer and facial recognition that determines the position of an electronic communication device (such as a laptop) are disclosed. The bracket 4100 that has been designed has calibration numbers 4102 that is used to help determine the size of the cell phone for accurate calibration. The bracket 4100 fits on the electronic communication device (such as a laptop monitor) by way of a pinch clamp. The plate on the bracket 4100 moves up and down with the phone on the cradle. The ergonomic program may have alarms and alert timer to indicate when to stretch during the day. It may have the capability to send an email with a certificate of completion wherever they chose the email to go.

According to some embodiments, the ergonomic steps process may direct the user to move up or down tilt on the smart phone screen. Further, it may give audible commands such as "move phone up" "tilt screen back" etc. to the user.

Further, a device with the electronics may also contain a touch plate (engineered into the device) that is used to determine when the device is in active use. This touch plate may be placed in strategic places in the device or on the phone or PDA surfaces. Further, thermal sensors may be used to sense when the device is in use. However, the touch plate may be built-in for cost-effectiveness. Further, the touch plate increases battery life and yields more data accuracy.

Further, parental monitoring features may help in making the data accessible to another user (presumably the parent).

Figure 45:
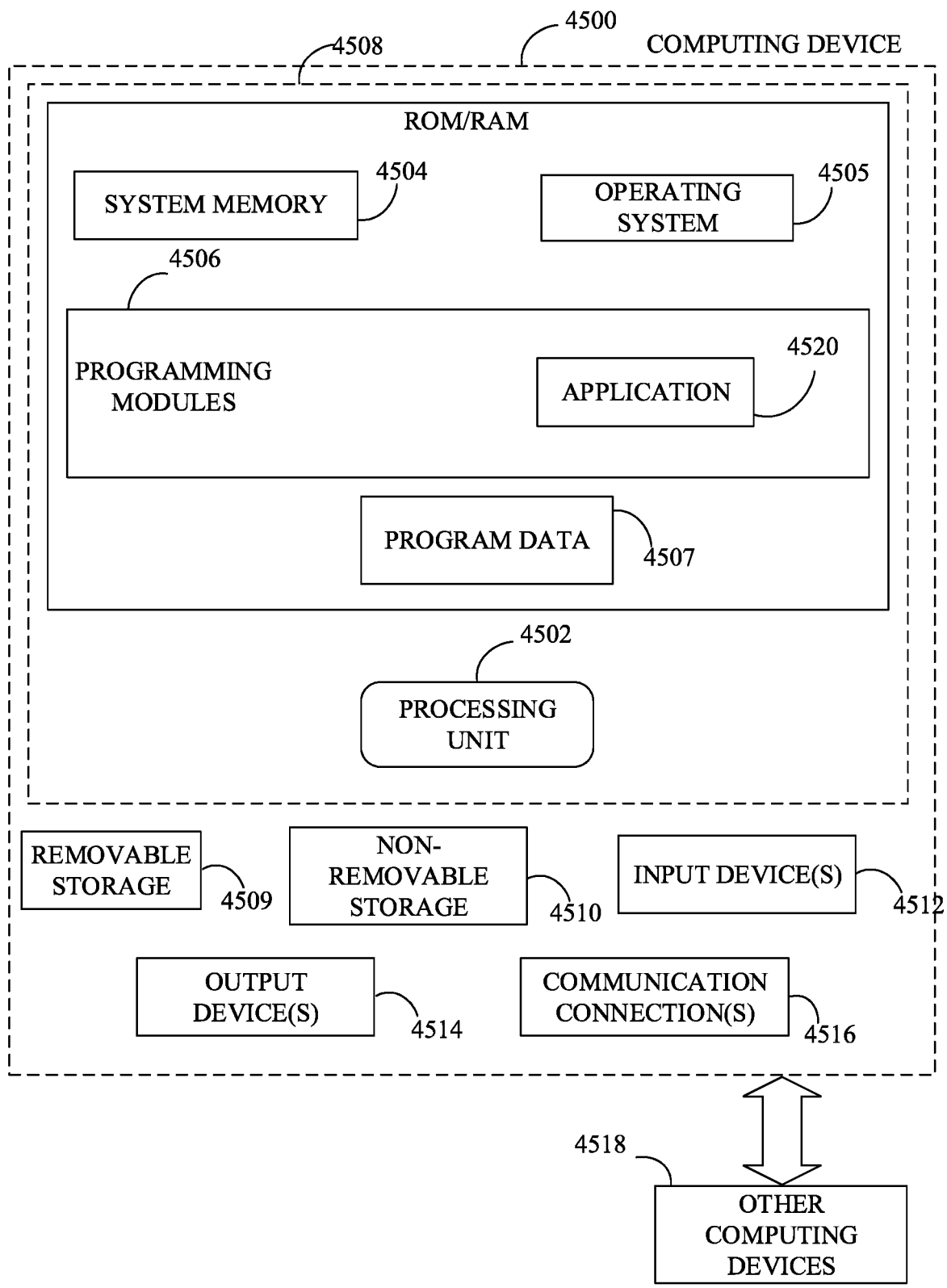
FIG. 45 is a block diagram of a computing device for implementing the methods disclosed herein, in accordance with some embodiments.

With reference to FIG. 45, a system consistent with an embodiment of the disclosure may include a computing device or cloud service, such as computing device 4500. In a basic configuration, computing device 4500 may include at least one processing unit 4502 and a system memory 4504. Depending on the configuration and type of computing device, system memory 4504 may comprise, but is not limited to, volatile (e.g. random-access memory (RAM)), non-volatile (e.g. read-only memory (ROM)), flash memory, or any combination. System memory 4504 may include operating system 4505, one or more programming modules 4506, and may include a program data 4507. Operating system 4505, for example, may be suitable for controlling computing device 4500's operation. In one embodiment, programming modules 4506 may include the image-processing module, machine learning module. Furthermore, embodiments of the disclosure may be practiced in conjunction with a graphics library, other operating systems, or any other application program and is not limited to any particular application or system. This basic configuration is illustrated in FIG. 45 by those components within a dashed line 4508.

Computing device 4500 may have additional features or functionality. For example, the computing device 4500 may also include additional data storage devices (removable and/or non-removable) such as, for example, magnetic disks, optical disks, or tape. Such additional storage is illustrated in FIG. 45 by a removable storage 4509 and a non-removable storage 4510. Computer storage media may include volatile and non-volatile, removable and non-removable media implemented in any method or technology for storage of information, such as computer-readable instructions, data structures, program modules, or other data. System memory 4504, removable storage 4509, and non-removable storage 4510 are all computer storage media examples (i.e., memory storage.) Computer storage media may include, but is not limited to, RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store information and which can be accessed by computing device 4500. Any such computer storage media may be part of device 4500. Computing device 4500 may also have input device(s) 4512 such as a keyboard, a mouse, a pen, a sound input device, a touch input device, a location sensor, a camera, a biometric sensor, etc. Output device(s) 4514 such as a display, speakers, a printer, etc. may also be included. The aforementioned devices are examples and others may be used.

Computing device 4500 may also contain a communication connection 4516 that may allow device 4500 to communicate with other computing devices 4518, such as over a network in a distributed computing environment, for example, an intranet or the Internet. Communication connection 4516 is one example of communication media. Communication media may typically be embodied by computer-readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media. The term computer-readable media as used herein may include both storage media and communication media.

As stated above, a number of program modules and data files may be stored in system memory 4504, including operating system 4505. While executing on processing unit 4502, programming modules 4506 (e.g., application 4520 such as a media player) may perform processes including, for example, one or more stages of methods, algorithms, systems, applications, servers, databases as described above. The aforementioned process is an example, and processing unit 4502 may perform other processes.

Generally, consistent with embodiments of the disclosure, program modules may include routines, programs, components, data structures, and other types of structures that may perform particular tasks or that may implement particular abstract data types. Moreover, embodiments of the disclosure may be practiced with other computer system configurations, including hand-held devices, general-purpose graphics processor-based systems, multiprocessor systems, microprocessor-based or programmable consumer electronics, application-specific integrated circuit-based electronics, minicomputers, mainframe computers, and the like. Embodiments of the disclosure may also be practiced in distributed computing environments where tasks are performed by remote processing devices that are linked through a communications network. In a distributed computing environment, program modules may be located in both local and remote memory storage devices.

Furthermore, embodiments of the disclosure may be practiced in an electrical circuit comprising discrete electronic elements, packaged or integrated electronic chips containing logic gates, a circuit utilizing a microprocessor, or on a single chip containing electronic elements or microprocessors. Embodiments of the disclosure may also be practiced using other technologies capable of performing logical operations such as, for example, AND, OR, and NOT, including but not limited to mechanical, optical, fluidic, and quantum technologies. In addition, embodiments of the disclosure may be practiced within a general-purpose computer or in any other circuits or systems.

Embodiments of the disclosure, for example, may be implemented as a computer process (method), a computing system, or as an article of manufacture, such as a computer program product or computer-readable media. The computer program product may be a computer storage media readable by a computer system and encoding a computer program of instructions for executing a computer process. The computer program product may also be a propagated signal on a carrier readable by a computing system and encoding a computer program of instructions for executing a computer process. Accordingly, the present disclosure may be embodied in hardware and/or in software (including firmware, resident software, micro-code, etc.). In other words, embodiments of the present disclosure may take the form of a computer program product on a computer-usable or computer-readable storage medium having computer-usable or computer-readable program code embodied in the medium for use by or in connection with an instruction execution system. A computer-usable or computer-readable medium may be any medium that can contain, store, communicate, propagate, or transport the program for use by or in connection with the instruction execution system, apparatus, or device.

The computer-usable or computer-readable medium may be, for example, but not limited to, an electronic, magnetic, optical, electromagnetic, infrared, or semiconductor system, apparatus, device, or propagation medium. More specific computer-readable medium examples (a non-exhaustive list), the computer-readable medium may include the following: an electrical connection having one or more wires, a portable computer diskette, a random-access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Embodiments of the present disclosure, for example, are described above with reference to block diagrams and/or operational illustrations of methods, systems, and computer program products according to embodiments of the disclosure. The functions/acts noted in the blocks may occur out of the order as shown in any flowchart. For example, two blocks shown in succession may in fact be executed substantially concurrently or the blocks may sometimes be executed in the reverse order, depending upon the functionality/acts involved.

While certain embodiments of the disclosure have been described, other embodiments may exist. Furthermore, although embodiments of the present disclosure have been described as being associated with data stored in memory and other storage mediums, data can also be stored on or read from other types of computer-readable media, such as secondary storage devices, like hard disks, solid-state storage (e.g., USB drive), or a CD-ROM, a carrier wave from the Internet, or other forms of RAM or ROM. Further, the disclosed methods' stages may be modified in any manner, including by reordering stages and/or inserting or deleting stages, without departing from the disclosure.

Although the present disclosure has been explained in relation to its preferred embodiment, it is to be understood that many other possible modifications and variations can be made without departing from the spirit and scope of the disclosure.

The following is claimed:

1. A device comprising a user interface, wherein the device is configured for facilitating correcting of a posture of a user based on an interaction between the user and the device through the user interface, wherein the interaction facilitates communication between the device and the user through the user interface, wherein the device comprises:
   at least one sensor configured for generating sensor data based on a spatial attribute of the device in relation to the user, wherein the spatial attribute comprises at least one of a spatial position of the device in relation to the user and a spatial orientation of the device in relation to the user;
   a processing device communicatively coupled to the at least one sensor, wherein the processing device is configured for:
      comparing the sensor data based on at least one predetermined criterion of the spatial attribute; and
      generating a command based on the comparing of the sensor data;
   a storage device communicatively coupled with the processing device, wherein the storage device is configured for storing the at least one predetermined criterion;
   an output indication device communicatively coupled with the processing device, wherein the output indication device is configured for generating at least one indication based on the command;
   a communication device communicatively coupled with the processing device, wherein the communication device is configured for:
      transmitting a plurality of questions to an output device of the user interface, wherein the plurality of questions includes a pain level and an area of pain; and
      receiving a plurality of information corresponding to the plurality of questions from an input device of the user interface;
   wherein the processing device is further configured for:
      analyzing the plurality of information;
      determining at least one outcome based on the analyzing of the plurality of information; and
      generating the at least one predetermined criterion based on the determining, wherein the storing of the at least one predetermined criterion is based on the generating of the at least one predetermined criterion;
   at least one touch sensor configured for generating second sensor data when touched by the user;
   the at least one touch sensor is externally mounted onto the device;
   wherein the processing device is configured for:
      analyzing the second sensor data to rule out false positive readings in order to identify an active use state; and
      generating a first command based on the analyzing of the second sensor data if the active use state is identified, wherein the at least one sensor is associated with a first state and a second state, wherein the at least one sensor is configured for transitioning between the first state and the second state based on the first command, wherein the at least one sensor generates the sensor data in the first state and the at least one sensor does not generate the sensor data in the second state;
   an orientation measuring circuit comprising at least one first orientation switch, at least one second orientation switch, a blocking diode, a leveling diode, and a light emitting diode;
   wherein the orientation-measuring circuit is configured for:
      turning on the at least one first orientation switch when the device is tilted up to 60-degrees in a vertical direction;
      turning on the at least one second orientation switch when the device is tilted up to 60-degrees in a horizontal direction;
      using the blocking diode to prevent the flow of reverse current in the orientation-measuring circuit; and
      using the leveling capacitor to detect the inclination and tilt of the device;
   wherein the at least one first orientation switch being at least one first inclinometer;
   wherein the at least one second orientation switch being at least one second inclinometer; and
   the at least one second inclinometer being oriented perpendicular to the at least one first inclinometer.

2. The device of claim 1, wherein the output indication device comprises at least one light-emitting device, wherein the at least one indication comprises light, wherein the at least one light-emitting device is configured for generating the light based on the command.

3. The device of claim 1, wherein the output indication device comprises at least one haptic motor, wherein the at least one indication comprises vibration, wherein the at least one haptic motor is configured for generating the vibration based on the command.

4. The device of claim 1, wherein the output indication device comprises at least one sound generating device, wherein the at least one indication comprises sound, wherein the at least one sound generating device is configured for generating the sound based on the command.

5. The device of claim 1, wherein the processing device is configured for:
   analyzing the sensor data;
   generating at least one analytic data based on the analyzing, wherein the device further comprises a communication device communicatively coupled with the processing device, wherein the communication device is configured for transmitting the at least one analytic data to at least one external device.

6. The device of claim 1, wherein the at least one sensor is configured for generating first sensor data based on a user spatial attribute of the user in relation to the user interface, wherein the user spatial attribute comprises at least one of a user position of the user in relation to the user interface and a user orientation of the user in relation to the user interface, wherein the processing device is configured for determining a spatial relationship between the user and the user interface, wherein the generating of the command is based on the determining.

7. The device of claim 6, wherein the processing device is configured for generating a notification based on the determining, wherein the notification comprises a correctness of the spatial relationship between the user and the user interface, wherein the user interface comprises a presentation device configured for presenting the notification to the user.

8. The device of claim 1 further comprises at least one external device coupled with the processing device, wherein the at least one external device is configured for generating at least one information based on a posture of the user in relation to the user interface, wherein the processing device is configured for:
    analyzing the at least one information; and
    determining a correct posture of the user in relation to the user interface based on the analyzing of the at least one information, wherein the generating of the command is based on the determining of the correct posture.

9. The device of claim 8, wherein the at least one external device is detachably attachable to at least one body part of the user using at least one attachment.

10. The device of claim 1 further comprising at least one dedicated mechanism detachably attached to the device, wherein the at least one dedicated mechanism is configured for detachably attaching the device to at least one object, wherein an object spatial attribute of the at least one object in relation to the user corresponds to the spatial attribute of the device.

11. A device comprising a user interface, wherein the device is configured for facilitating correcting of a posture of a user based on an interaction between the user and the device through the user interface, wherein the interaction facilitates communication between the device and the user through the user interface, wherein the device comprises:
    at least one sensor configured for generating sensor data based on a spatial attribute of the device in relation to the user, wherein the spatial attribute comprises at least one of a spatial position of the device in relation to the user and a spatial orientation of the device in relation to the user;
    a processing device communicatively coupled to the at least one sensor, wherein the processing device is configured for:
        comparing the sensor data based on at least one predetermined criterion of the spatial attribute;
        generating a command based on the comparing of the sensor data;
        analyzing the sensor data; and
        generating at least one analytic data based on the analyzing;
    a storage device communicatively coupled with the processing device, wherein the storage device is configured for storing the at least one predetermined criterion of the spatial attribute;
    a communication device communicatively coupled with the processing device, wherein the communication device is configured for transmitting the at least one analytic data to at least one external device;
    an output indication device communicatively coupled with the processing device, wherein the output indication device is configured for generating at least one indication based on the command;
    wherein the communication device is further configured for:
        transmitting a plurality of questions to an output device of the user interface, wherein the plurality of questions includes a pain level and an area of pain; and
        receiving a plurality of information corresponding to the plurality of questions from an input device of the user interface;
    wherein the processing device is further configured for:
        analyzing the plurality of information;
        determining at least one outcome based on the analyzing of the plurality of information;
    generating the at least one predetermined criterion based on the determining, wherein the storing of the at least one predetermined criterion is based on the generating of the at least one predetermined criterion;
        at least one touch sensor configured for generating second sensor data when touched by the user;
        the at least one touch sensor is externally mounted onto the device;
    wherein the processing device is configured for:
    analyzing the second sensor data to rule out false positive readings in order to identify an active use state; and
        generating a first command based on the analyzing of the second sensor data if the active use state is identified, wherein the at least one sensor is associated with a first state and a second state, wherein the at least one sensor is configured for transitioning between the first state and the second state based on the first command, wherein the at least one sensor generates the sensor data in the first state and the at least one sensor does not generate the sensor data in the second state;
    an orientation measuring circuit comprising at least one first orientation switch, at least one second orientation switch, a blocking diode, a leveling diode, and a light emitting diode;
    wherein the orientation-measuring circuit is configured for:
    turning on the at least one first orientation switch when the device is tilted up to 60-degrees in a vertical direction;
    turning on the at least one second orientation switch when the device is tilted up to 60-degrees in a horizontal direction;
    using the blocking diode to prevent the flow of reverse current in the orientation-measuring circuit; and
    using the leveling capacitor to detect the inclination and tilt of the device;
    wherein the at least one first orientation switch being at least one first inclinometer;
    wherein the at least one second orientation switch being at least one second inclinometer; and
    the at least one second inclinometer being oriented perpendicular to the at least one first inclinometer.

12. The device of claim 11, wherein the output indication device comprises at least one light-emitting device, wherein the at least one indication comprises light, wherein the at least one light-emitting device is configured for generating the light based on the command.

13. The device of claim 11, wherein the output indication device comprises at least one haptic motor, wherein the at least one indication comprises vibration, wherein the at least one haptic motor is configured for generating the vibration based on the command.

14. The device of claim 11, wherein the output indication device comprises at least one sound generating device, wherein the at least one indication comprises sound, wherein the at least one sound generating device is configured for generating the sound based on the command.

15. The device of claim 11, wherein the at least one sensor is configured for generating first sensor data based on a user spatial attribute of the user in relation to the user interface, wherein the user spatial attribute comprises at least one of a user position of the user in relation to the user interface and a user orientation of the user in relation to the user interface, wherein the processing device is configured for determining a spatial relationship between the user and the user interface, wherein the generating of the command is based on the determining.

16. The device of claim 11 further comprises at least one external device coupled with the processing device, wherein the at least one external device is configured for generating at least one information based on a posture of the user in relation to the user interface, wherein the processing device is configured for:
analyzing the at least one information; and
determining a correct posture of the user in relation to the user interface based on the analyzing of the at least one information, wherein the generating of the command is based on the determining of the correct posture.

17. The device of claim 11 further comprising at least one first sensor communicatively coupled with the processing device, wherein the at least one first sensor is configured for generating second sensor data based on at least one action performed by the user, wherein the processing device is configured for:
analyzing the second sensor data; and
generating a first command based on the analyzing of the second sensor data, wherein the at least one sensor is associated with a first state and a second state, wherein the at least one sensor is configured for transitioning between the first state and the second state based on the first command, wherein the at least one sensor generates the sensor data in the first state and the at least one sensor does not generate the sensor data in the second state.

18. A portable electronic device comprising a display device, wherein the portable electronic device is configured for facilitating correcting of a posture of a user based on an interaction between the user and the portable electronic device through the display device, wherein the interaction facilitates communication between the portable electronic device and the user through the display device, wherein the portable electronic device comprises:
at least one sensor configured for generating sensor data based on an orientation of the device in relation to a horizontal level, wherein the orientation comprises an angle of inclination in relation to the horizontal level;
a processing device communicatively coupled to the at least one sensor, wherein the processing device is configured for:
comparing the sensor data based on at least one predetermined orientation range, wherein the at least one predetermined orientation range is between 0 degrees of inclination in relation to the horizontal level and 90 degrees of inclination in relation to the horizontal level; and
generating a command based on the comparing of the sensor data;
a storage device communicatively coupled with the processing device, wherein the storage device is configured for storing the at least one predetermined orientation range;
a haptic motor communicatively coupled with the processing device, wherein the haptic motor is configured for generating vibration based on the command;
a communication device communicatively coupled with the processing device, wherein the communication device is further configured for:
transmitting a plurality of questions to an output device of the display device, wherein the plurality of questions includes a pain level and an area of pain; and
receiving a plurality of information corresponding to the plurality of questions from an input device of the display device;
wherein the processing device is further configured for:
analyzing the plurality of information;
determining at least one outcome based on the analyzing of the plurality of information;
generating the at least one predetermined criterion based on the determining, wherein the storing of the at least one predetermined criterion is based on the generating of the at least one predetermined criterion;
at least one touch sensor configured for generating second sensor data when touched by the user;
the at least one touch sensor is externally mounted onto the device;
wherein the processing device is configured for:
analyzing the second sensor data to rule out false positive readings in order to identify an active use state; and
generating a first command based on the analyzing of the second sensor data if the active use state is identified, wherein the at least one sensor is associated with a first state and a second state, wherein the at least one sensor is configured for transitioning between the first state and the second state based on the first command, wherein the at least one sensor generates the sensor data in the first state and the at least one sensor does not generate the sensor data in the second state;
an orientation measuring circuit comprising at least one first orientation switch, at least one second orientation switch, a blocking diode, a leveling diode, and a light emitting diode;
wherein the orientation-measuring circuit is configured for:
turning on the at least one first orientation switch when the device is tilted up to 60-degrees in a vertical direction;
turning on the at least one second orientation switch when the device is tilted up to 60-degrees in a horizontal direction;
using the blocking diode to prevent the flow of reverse current in the orientation-measuring circuit; and
using the leveling capacitor to detect the inclination and tilt of the device;
wherein the at least one first orientation switch being at least one first inclinometer;
wherein the at least one second orientation switch being at least one second inclinometer; and the at least one second inclinometer being oriented perpendicular to the at least one first inclinometer.

* * * * *